(12) United States Patent
Crockett et al.

(10) Patent No.: US 8,744,982 B2
(45) Date of Patent: Jun. 3, 2014

(54) GENE-SPECIFIC PREDICTION

(75) Inventors: David K. Crockett, South Jordan, UT (US); Perry G. Ridge, Orem, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 232 days.

(21) Appl. No.: 13/471,294

(22) Filed: May 14, 2012

(65) Prior Publication Data
US 2012/0310863 A1    Dec. 6, 2012

Related U.S. Application Data

(60) Provisional application No. 61/518,833, filed on May 12, 2011.

(51) Int. Cl.
*G06N 5/04* (2006.01)

(52) U.S. Cl.
CPC ............ *G06N 5/046* (2013.01); *C12Q 2500/00* (2013.01)
USPC .............................................. 706/12; 706/45

(58) Field of Classification Search
CPC ........................... G06N 5/046; C12Q 2500/00
USPC ..................................................... 706/12, 45
See application file for complete search history.

(56) References Cited

U.S. PATENT DOCUMENTS

2004/0137436 A1    7/2004 Larder et al.
2006/0278241 A1   12/2006 Ruano
2009/0177496 A1    7/2009 Tuck et al.

OTHER PUBLICATIONS

Huang, et al., Mutation Screening of AP3M2 in Japanese Epilepsy Patients, Brain & Development 29, 2007, pp. 462-467.*

* cited by examiner

*Primary Examiner* — Wilbert L Starks
(74) *Attorney, Agent, or Firm* — James W. Hill; McDermott Will & Emery LLP

(57) ABSTRACT

A gene-specific prediction tool for classifying and interpreting gene tests is described. The prediction tool includes a classifier trained and tested using databases of gene variants and their known phenotypes. The classifier uses differences between features of amino acids in obtaining attributes used to perform classification and generate predictions, including for benign and pathologic outcomes, for uncertain gene variants.

16 Claims, 19 Drawing Sheets

| Gene Symbol<br>Biological Function | Gene Name<br>Disease Association | Curated<br>Variants | Exonic<br>nsSNPs |
|---|---|---|---|
| ACVRL1<br>activin receptor activity, type 1 | activin A receptor type II-like 1<br>hereditary hemorrhagic telangiectasia | 332 | 192 |
| AIP<br>transcription coactivator activity | aryl hydrocarbon receptor interacting protein<br>familial pituitary adenoma | 102 | 84 |
| BTD<br>biotin carboxylase activity | biotinid ase<br>biotinidase deficiency | 155 | 105 |
| CFTR<br>chloride channel regulator activity | cystic fibrosis transmembrane conductance regulator<br>cystic fibrosis | 252 | 121 |
| COL4A5<br>extracellular matrix structural constituent | collagen, type IV, alpha 5<br>X-linked Alport syndrome (hereditary nephritis) | 600 | 266 |
| ENG<br>TGF β receptor activity | endoglin<br>hereditary hemorrhagic telangiectasia | 397 | 124 |
| GALT<br>uridylyltransferase activity | galastose-1- phosphate uridylyltransferase<br>galactosamia | 247 | 168 |
| GJB2<br>gap junction channel activity | gap junction protein, beta 2 ( connexin 26)<br>hereditary sensorineural hearing loss | 61 | 43 |
| MECP2<br>transcription co-repressor activity | methyl CpG binding protein 2<br>Rett Syndrome | 26 | 14 |
| MSH2<br>guanine/ thymine mispair binding | mut5 homolog 2<br>hereditary nonpolyposis colonrectal cancer | 89 | 8 |

FIG. 4B -1

| Gene Symbol<br>Biological Function | Gene Name<br>Disease Association | Curated<br>Variants | Exonic<br>nsSNPs |
|---|---|---|---|
| MSH6<br>guanine/thymine mispair binding | mut5 homolog 6<br>hereditary nonpolyposis colonrectal cancer | 34 | 10 |
| NF1<br>Ras GTPase activator activity | neurofibromin 1<br>neurofibromatosis type 1 | 125 | 121 |
| PAH<br>phenylalanine catabolism | phenylalanine hydroxylase<br>phenylketonuria (PKU) | 730 | 126 |
| PLOD1<br>procollagen-lysine-dioxygenase activity | procollagen-lysine 1, 2-oxoglutarate 5-dioxygenase 1<br>Ehlers-Danlos syndrome type VI | 34 | 12 |
| PMS2<br>mismatched DNA binding | postmeiotic segregation increased 2<br>hereditary nonpalyposis colonrectal cancer | 348 | 45 |
| RET<br>transmembrane receptor kinase activity | ret proto-oncogene<br>multiple endocrine neoplasia, medullary thyroid carcinoma | 146 | 97 |
| SLC22A5<br>carnitine transporter activity | solute carrier family 22, member 5<br>primary carnitine deficiency | 95 | 57 |
| SMAD4<br>transcription activator activity | SMAD family member 4<br>juvenile polyposis syndrome, pancreatic cancer | 86 | 23 |
| SPINK1<br>endopeptidase inhibitor activity | serine peptidase inhibitor, Kazal type 1<br>hereditary pancreatitis | 73 | 5 |
| SPRED1<br>inactivation of MAPK activity | sprouty-related, EVH1 domain containing 1<br>Legius-syndrome (neurofibromatosis type-like syndrome) | 54 | 18 |

FIG. 4B -2

| CLASSIFIER | ALGORITHM SENSITIVITY | ALGORITHM SPECIFICITY | % POSITIVE PREDICTIVE VALUE |
|---|---|---|---|
| ZeroR | 1.00 | 0.00 | 55.7% |
| NEAREST NEIGHBOR | 0.896 | 0.674 | 77.6% |
| RANDOM FOREST | 0.776 | 0.739 | 78.9% |
| SUPPORT VECTOR MACHINE | 0.914 | 0.696 | 79.1% |
| SIMPLE LOGISTIC | 0.826 | 0.761 | 81.4% |
| NAÏVE BAYESIAN | 0.827 | 0.783 | 82.7% |
| POLYPHEN | 0.597 | 0.920 | 54.1% |
| SIFT | 0.816 | 0.821 | 77.9% |
| MUTPRED | 0.767 | 0.823 | 84.3% |
| PMuT | 0.783 | 0.591 | 72.3% |
| PSAAP PREDICTION | 0.938 | 0.867 | 88.3% |

FIG. 7

|             | PSAAP | MUTPRED | POLYPHEN | PMUT  | SIFT  |
|-------------|-------|---------|----------|-------|-------|
| SENSITIVITY | 0.938 | 0.767   | 0.597    | 0.783 | 0.816 |
| SPECIFICITY | 0.867 | 0.823   | 0.920    | 0.591 | 0.821 |
| PRECISION   | 0.883 | 0.843   | 0.541    | 0.723 | 0.779 |

FIG. 8A

| Gene | PSAAP[a] | All_gene[b] | SIFT[c] | PolyPhen[d] | PMut[e] | MutPred[f] |
|---|---|---|---|---|---|---|
| ACVRL1 | 88 | 77 | 57 | 67 | 69 | 81 |
| AIP | 91 | 71 | 71 | 73 | 80 | 79 |
| BTO | 91 | 79 | 77 | 72 | 71 | 87 |
| CFTR | 90 | 63 | 68 | 74 | 70 | 89 |
| COL4A5 | 88 | 82 | 58 | 74 | 62 | 73 |
| ENG | 92 | 83 | 62 | 64 | 73 | 65 |
| GALT | 86 | 77 | 66 | 65 | 58 | 87 |
| GIB2 | 87 | 77 | 69 | 74 | 67 | 83 |
| NF1 | 89 | 70 | 64 | 70 | 70 | 84 |
| PAH | 89 | 80 | 59 | 76 | 77 | 84 |
| PMS2 | 88 | 63 | 64 | 74 | 74 | 72 |
| RET | 94 | 84 | 78 | 54 | 72 | 84 |
| SLC22A5 | 90 | 82 | 74 | 76 | 53 | 82 |
| SMAD4 | 84 | 82 | 71 | 70 | 85 | 86 |
| SPRED1 | 93 | 86 | 71 | 65 | 56 | 71 |
| (avg) | 89.3 | 77.1 | 67.3 | 69.9 | 69.1 | 80.5 |
| (min) | 84.0 | 63.0 | 57.0 | 54.0 | 53.0 | 65.0 |
| (max) | 94.0 | 86.0 | 78.0 | 76.0 | 85.0 | 89.0 |

[a] Primary Sequence Amino Acid Properties (PSMP) algorithm, gene-specific trained.
[b] Primary Sequence Amino Acid Properties (PSMP) algorithm, all-gene (n=20) trained.
[c] Analyzed with default settings at http://sift.jcvi.org.
[d] Analyzed with default settings at http://genetics.bwh.harvard.edu/pph.
[e] Analyzed with default settings at http://mmb.pcb.ub.es/PMut.
[f] Analyzed with default settings at http://mutdb.org/mutpred.

FIG. 8B

|  | CfsSubset | RELIEF-F | SVM-RFE | OVERLAP |
|---|---|---|---|---|
| ACVRL1 | 7 | 39 | 49 | 7 |
| AIP | 90 | 29 | 117 | 135 |
| BTD | 41 | 20 | 39 | 8 |
| CFTR | 19 | 161 | 139 | 12 |
| COL4A5 | 63 | 65 | 88 | 21 |
| ENG | 13 | 82 | 59 | 9 |
| GALT | 46 | 40 | 45 | 35 |
| G1B2 | 11 | 37 | 145 | 11 |
| NF1 | 28 | 20 | 39 | 18 |
| PAH | 29 | 73 | 129 | 24 |
| PMS2 | 13 | 58 | 107 | 11 |
| RET | 87 | 56 | 47 | 9 |
| SLC22A5 | 76 | 96 | 87 | 13 |
| SMAD4 | 63 | 65 | 88 | 42 |
| SPRED1 | 59 | 44 | 31 | 27 |
| All GENE | 25 | 56 | 135 | 23 |

FIG. 8C

|  | ACVRL1 | AIP | BTD | CFTR | COL4A5 | ENG | GALT | GJB2 | NF1 | PAH | PMS2 | RET | SLC22A5 | SMAD4 | SPRED1 |
|---|---|---|---|---|---|---|---|---|---|---|---|---|---|---|---|
| ACVFL1 | 88 | 85 | 74 | 70 | 84 | 77 | 79 | 79 | 85 | 74 | 76 | 80 | 81 | 72 | 78 |
| AIP | 72 | 91 | 62 | 62 | 69 | 59 | 66 | 55 | 68 | 57 | 65 | 63 | 62 | 58 | 62 |
| BTD | 77 | 79 | 91 | 77 | 85 | 73 | 82 | 81 | 85 | 76 | 70 | 70 | 71 | 81 | 85 |
| CFTR | 53 | 62 | 56 | 90 | 56 | 54 | 59 | 55 | 51 | 54 | 47 | 60 | 53 | 57 | 61 |
| COL4A5 | 47 | 58 | 62 | 51 | 88 | 83 | 55 | 61 | 52 | 57 | 46 | 56 | 57 | 56 | 50 |
| ENG | 48 | 47 | 62 | 57 | 84 | 92 | 49 | 55 | 51 | 56 | 50 | 60 | 54 | 60 | 61 |
| GALT | 83 | 82 | 85 | 80 | 77 | 74 | 86 | 77 | 80 | 81 | 85 | 80 | 81 | 77 | 84 |
| GJB2 | 67 | 56 | 73 | 54 | 56 | 70 | 73 | 87 | 55 | 66 | 69 | 64 | 62 | 56 | 71 |
| NF1 | 90 | 76 | 84 | 75 | 90 | 89 | 75 | 79 | 89 | 83 | 75 | 73 | 78 | 81 | 84 |
| PAH | 62 | 74 | 59 | 55 | 63 | 58 | 64 | 60 | 82 | 89 | 58 | 71 | 65 | 60 | 59 |
| PMS2 | 66 | 62 | 63 | 61 | 61 | 70 | 55 | 69 | 62 | 71 | 88 | 66 | 70 | 63 | 56 |
| RET | 84 | 69 | 62 | 42 | 64 | 57 | 46 | 72 | 66 | 72 | 45 | 94 | 49 | 68 | 59 |
| SLC22A5 | 74 | 66 | 63 | 73 | 72 | 71 | 69 | 68 | 73 | 70 | 68 | 52 | 82 | 71 | 81 |
| SMAD4 | 49 | 53 | 65 | 61 | 49 | 64 | 47 | 53 | 67 | 67 | 56 | 86 | 64 | 84 | 67 |
| SPRED1 | 82 | 85 | 85 | 87 | 87 | 87 | 80 | 84 | 81 | 83 | 77 | 86 | 84 | 80 | 93 |

FIG. 8D

| RETuncertain gene variant | PSAAP Prediction[a] | Mut Pred Prediction[b] | PolyPhen Prediction[c] | SIFT Prediction[d] | PMut Prediction[e] |
|---|---|---|---|---|---|
| 5/5 agreement | | | | | |
| A510V | benign | benign | benign | tolerated | neutral |
| R600Q | benign | benign | benign | tolerated | neutral |
| K603Q | benign | benign | benign | tolerated | neutral |
| E632K | benign | benign | benign | tolerated | neutral |
| A640G | benign | benign | benign | tolerated | neutral |
| V648I | benign | benign | benign | tolerated | neutral |
| Y791N | pathogenic | disrupted | probably damaging | affects function | pathological |
| E843D | benign | benign | benign | tolerated | neutral |
| R844L | pathogenic | disrupted | probably damaging | affects function | pathological |
| R844W | pathogenic | disrupted | probably damaging | affects function | pathological |
| R886W | pathogenic | disrupted | probably damaging | affects function | pathological |
| R912Q | pathogenic | disrupted | probably damaging | affects function | pathological |
| 4/5 agreement | | | | | |
| C611S | pathogenic | disrupted | probably damaging | affects function | neutral |
| D631G | pathogenic | benign | probably damaging | affects function | pathological |
| E805K | benign | disrupted | probably damaging | affects function | pathological |
| S819I | pathogenic | disrupted | probably damaging | affects function | neutral |
| R833C | pathogenic | benign | probably damaging | affects function | pathological |
| S904C | pathogenic | benign | probably damaging | affects function | pathological |
| S904F | pathogenic | benign | probably damaging | affects function | pathological |
| 3/5 agreement | | | | | |
| Y606C | pathogenic | benign | probably damaging | tolerated | pathological |
| C531R | pathogenic | benign | probably damaging | tolerated | pathological |
| G533S | pathogenic | benign | probably damaging | affects function | neutral |
| D631A | pathogenic | benign | probably damaging | affects function | neutral |
| D631V | pathogenic | benign | probably damaging | affects function | neutral |
| R635G | pathogenic | benign | probably damaging | tolerated | pathological |
| P841L | pathogenic | benign | probably damaging | tolerated | pathological |
| L881V | benign | disrupted | probably damaging | affects function | neutral |
| K907M | pathogenic | benign | probably damaging | affects function | neutral |
| 2/5 agreement | | | | | |
| C630S | pathogenic | benign | probably damaging | tolerated | neutral |
| D631E | benign | benign | probably damaging | tolerated | pathological |
| S649L | pathogenic | benign | probably damaging | tolerated | neutral |
| H665Q | benign | benign | probably damaging | tolerated | pathological |
| R844Q | benign | benign | probably damaging | tolerated | pathological |
| M848T | benign | benign | probably damaging | tolerated | pathological |
| I852M | benign | benign | probably damaging | affects function | neutral |
| K907E | benign | benign | probably damaging | affects function | neutral |
| 1/5 agreement | | | | | |
| G321R | benign | benign | benign | tolerated | pathological |
| E511K | benign | benign | benign | tolerated | pathological |
| D631N | benign | benign | benign | tolerated | pathological |
| A641S | benign | benign | possibly damaging | tolerated | neutral |
| K666N | benign | benign | probably damaging | tolerated | neutral |
| R770Q | benign | benign | probably damaging | tolerated | neutral |
| N777S | benign | benign | possibly damaging | tolerated | neutral |
| V778I | benign | benign | benign | affects function | neutral |
| E818K | benign | benign | possibly damaging | tolerated | neutral |

[a] Primary Sequence Amino Acid Properties (PSAAP) algorithm
[b] Analyzed with default settings at http:// mutdb.orf/mutpred.
[c] Analyzed with default settings at http:// geneticsbwh.harvard.edu/pph.
[d] Analyzed with default settings at http:// sift.jcvi.org
[e] Analyzed with default settings at http:// mmb.pcb.ub.es/Pmut

FIG. 9A

| RET GENE VARIANT CURATED OUTCOME | POLYPHEN PREDICTION | SIFT PREDICTION | MUTPRED PREDICTION |
|---|---|---|---|
| G533C (PATHOGENIC) | PROBABLY DAMAGING | AFFECTS FUNCTION | NOT AVAILABLE |
| C609S (UNCERTAIN) | PROBABLY DAMAGING | AFFECTS FUNCTION | DELETERIOUS (0.90) |
| C611S (PATHOGENIC) | PROBABLY DAMAGING | AFFECTS FUNCTION | DELETERIOUS (0.90) |
| C618G (PATHOGENIC) | PROBABLY DAMAGING | TOLERATED | DELETERIOUS (0.88) |
| C620R (PATHOGENIC) | BENIGN | TOLERATED | DELETERIOUS (0.75) |
| C630R (PATHOGENIC) | PROBABLY DAMAGING | TOLERATED | DELETERIOUS (0.70) |
| D631Y (PATHOGENIC) | PROBABLY DAMAGING | AFFECTS FUNCTION | DELETERIOUS (0.69) |
| C634L (PATHOGENIC) | PROBABLY DAMAGING | TOLERATED | DELETERIOUS (0.69) |
| S649L (PATHOGENIC) | PROBABLY DAMAGING | TOLERATED | DELETERIOUS (0.66) |
| G691S (BENIGN) | BENIGN | TOLERATED | BENIGN (0.20) |

FIG. 9B

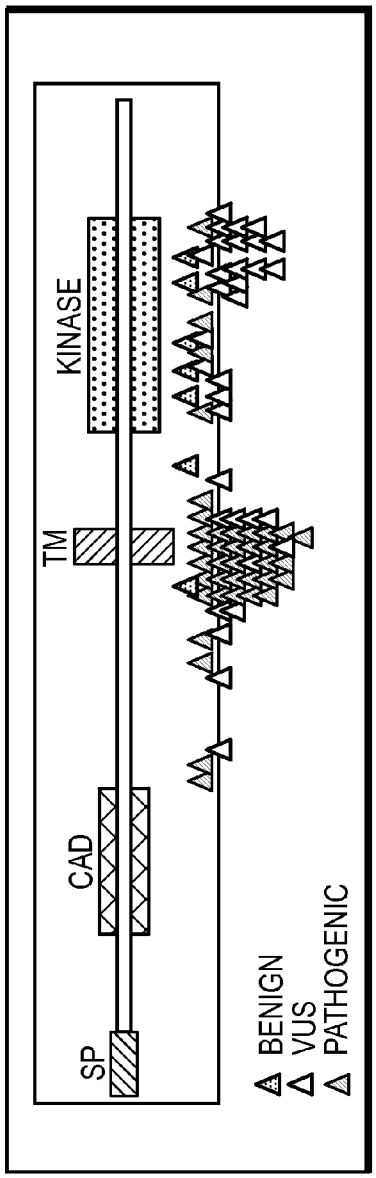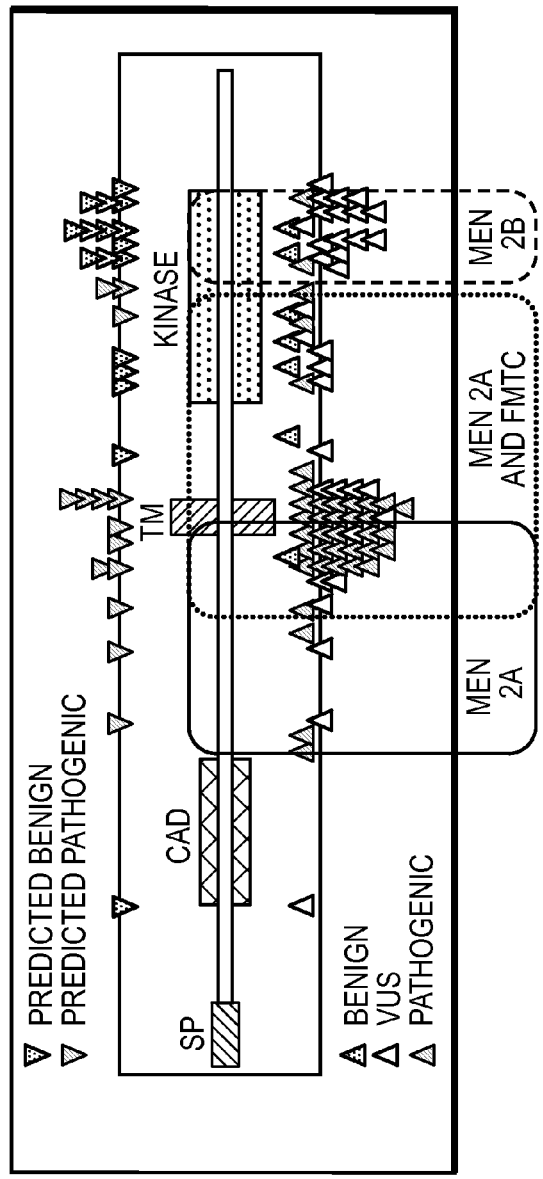

GENE-SPECIFIC PREDICTION

RELATED APPLICATIONS

The present application claims the benefit of priority under 35 U.S.C. §119 from U.S. Provisional Patent Application Ser. No. 61/518,833 entitled "Decision Support for Uncertain Gene Variants," filed on May 12, 2011, which is hereby incorporated by reference in its entirety for all purposes.

BACKGROUND

Medical genetics involves diagnosis, management, and determination of risk of hereditary disorders. Understanding the genotype-phenotype correlation of gene variants in disease is a major component of medical genetics. In monogenic diseases, gene mutations are typically curated as either "pathogenic" or "benign." However, many gene variants (i.e., gene mutations) are classified as being "unknown" or "uncertain" because they cannot be clearly associated with a clinical phenotype. Accurate interpretation of gene testing, including accurate phenotype association of gene variants, is an important component in customization of healthcare such that decisions and practices provided to a patient are tailored to the individual patient.

In the recent years, various efforts, such as the Human Variome Project, 1000 Genomes, and NCBI Genetic Testing Registry, have resulted in a growing interest in annotation and clinical interpretation of gene variants in human diseases. Further, with rapidly evolving technologies (e.g., Single Nucleotide Polymorphisms (SNP) chip genome wide association studies and next-generation sequencing), genomic analysis has become faster and more cost effective, yielding much larger data sets than previously available. However, there exists a gap between the rapidly growing collections of genetic variation (i.e., genetic mutation) and practical clinical implementation. Further, as genetic information is incorporated into the electronic medical record, new decision support approaches are needed to provide clinicians with a preferred course of treatment. Moreover, for decision support rules to add value, the clinical relevance of laboratory information should be well understood.

Gene variant classification is critical in informing clinicians of the most appropriate course of treatment. To that end, medical geneticists typically rely on patient history and family segregation, literature review and trusted colleagues to stay informed of the phenotype consequences of a given gene variant. Although computer-based prediction methods may be employed to classify gene variants, there still exists a lack of a widely accepted standard computational predictor of mutation severity for novel or uncertain gene variants in clinical use. Further, existing prediction methods, despite being actively used in laboratories, do not offer sufficient accuracy to predict disease phenotype to the degree necessary to be clinically applicable.

In the recent years, updated recommendations on reporting and classification of gene variants, including approaches targeted at determining the clinical significance of variants of uncertain significance, have been proposed from the American College of Medical Geneticists (ACMG). Further, in order to improve interpretation of unclassified genetic variants, definitions and terminology have also been recommended by the International Agency for Research on Cancer (IARC).

Despite these recommendations, terms such as "deleterious," "mutation," "pathogenic," or "causative of disease" are still being used in reporting genetic tests. Further, test results such as "indeterminate," "unknown," "uncertain," "unclassified," or "undetermined" render interpretation of the significance of a gene test result difficult. Further compounding this issue, word modifiers such as "likely," "suspected," "predicted," "mild," "moderate," or "severe" often are used to accompany variant classification.

The lack of a quantitative metric or a standardized scale for evaluation of novel or uncertain gene variants render test result interpretation difficult and subjective to location and expertise at hand. A second and closely related challenge is the lack of an objective and standardized framework or context to make that metric meaningful. The quantitative metric and framework for evaluation become especially critical for interpretation of novel and uncertain gene variants where there is the obvious lack of traditional or existing evidence such as family history, pedigree trios or sib pairs, confirming literature reports, bench assay biochemical evidence, or colleague consensus of disease association.

SUMMARY

Certain embodiments of the present invention relate to predicting a result of genetic mutation. Differences between (i) values of a first plurality of features, of amino acids encoded by a variant of a wild-type polynucleotide sequence, and (ii) values of a second plurality of features, of amino acids encoded by the wild-type polynucleotide sequence are determined. The features of first plurality are the same as the features of the second plurality. Using the differences, a predicted phenotype severity of the variant may be determined.

In certain embodiments, the prediction may include an indication of a disease.

In some embodiments, at least one of the first plurality of features may be selected from the group consisting of alpha NH chemical shifts, normalized frequency of C terminal helix, normalized frequency of chain reversal R, normalized positional frequency at helix termini N2, partition coefficient Garel, relative preference value at C2, relative preference value at N1, weights for beta sheet at the window position of 0, amino acid distribution, average relative fractional occurrence in A0(i), average relative probability of inner beta sheet, composition, effective partition energy, free energy in alpha helical region, frequency of the third residue in turn, helix formation parameters (delta delta G), hydrophobicity, membrane buried preference parameters, normalized frequency of beta structure, normalized frequency of coil, normalized positional frequency at helix termini Cc, STERIMOL maximum width of the side chain, and Zimm Bragg parameter sigmax1.0E4.

Certain embodiments of the present invention relate to predicting a result of genetic mutation. Differences between (i) values of a first plurality of features, of amino acids encoded by a variant of a wild-type polynucleotide sequence, and (ii) values of a second plurality of features, of amino acids encoded by the wild-type polynucleotide sequence may be determined. The features of the first plurality are the same as the features of the second plurality. A machine learning classification algorithm may be trained using the differences and a prediction of phenotype severity of the gene variant may be obtained using the trained algorithm,.

Certain embodiments of the present invention relate to a gene-specific prediction tool for classifying and interpreting of a gene test. In one embodiment, a plurality of features of gene variants having known phenotype severity is selected and differences among values of the selected features and corresponding values of the plurality of features in wild type amino acids are determined. A machine learning classification algorithm may be trained using the determined differences and a prediction outcome of the machine learning classification algorithm may be reported.

Some embodiments include a method of predicting a result of genetic mutation, comprising: determining differences between (i) values of a first plurality of features, of amino acids, e.g., in a polypeptide, encoded by a variant of a wild-type polynucleotide sequence, and (ii) values of a second plurality of features, of amino acids encoded by the wild-type polynucleotide sequence; wherein the features of the first plurality are the same as the features of the second plurality; and by a processor and based on the differences, determining a predicted phenotype severity of the variant.

In some embodiments, a plurality of features of gene variants having known phenotype severity is selected and differences among values of the selected features and corresponding values of the plurality of features in wild type amino acids are determined. A machine learning classification algorithm may be trained using the determined differences. The trained machine learning classification algorithm may be used to predict phenotype severity of gene variants having uncertain phenotype severity and the predicted severity of gene variants having uncertain phenotype severity may be reported.

Machine learning classification algorithms, such as Zero Rules (ZeroR), naive Bayesian, Simple Logistic Regression (Simple Logistic), Support Vector Machine (SMO), k-nearest neighbor (IBk), or Random Forest Regression (Random Forest) may be used with the embodiments disclosed herein.

In certain embodiments, the gene variants having known phenotype severity may include at least one of Rearranged During Transformation (RET) type gene variants or curated non-synonymous RET mutations with known phenotype severity.

In some embodiments, the plurality of features may include at least one of physical, chemical, conformational, physiochemical, biochemical, and energetic properties of gene variants and wild type amino acids.

In some embodiments, the prediction outcome of the machine learning classification algorithm may be reported by providing an indication of phenotype severity of the gene variant. In some embodiments, the indication of the phenotype severity may include an indication of a predicted benign or pathogenic phenotype. In certain embodiments, the indication of phenotype severity may include an indication of an associated disease. In certain embodiments, the performance of the trained machine learning algorithm may be verified by comparing the indicated phenotype severity with the known phenotype severity.

In certain embodiments, determining the differences among values of the selected features and corresponding values of the plurality of features in wild type amino acids may include determining absolute value of the differences among values of the selected features and corresponding values of the plurality of features in wild type amino acids.

In certain embodiments, the plurality of features may be selected by performing correlation-based feature subset selection and best first greedy hill-climbing search and identifying a subset of properties that differentiate benign mutations from pathogenic mutations based on amino acid changes in RET.

The advantages and novel features are set forth in part in the description which follows, and in part will become apparent to those skilled in the art upon examination of the following and the accompanying drawings or may be learned by production or operation of the examples. The advantages of the present teachings may be realized and attained by practice or use of the methodologies, instrumentalities and combinations described herein.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology.

Accordingly, the drawings and detailed description are to be regarded as illustrative in nature and not as restrictive.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 4B is a table that includes a summary of clinically-curated gene variants that may be used with the embodiments disclosed herein.

FIG. 7 is a table that summarizes the performance of various classifiers, including a Primary Sequence Amino Acid Properties (PSAAP) classifier developed according to certain embodiments described herein, in interpreting gene test results using a dataset of RET gene variant-disease data.

FIG. 8A summarizes the performance of the PSAAP classifier in classifying RET curated mutations with known outcomes and compares its performance to other methods available in the art.

FIG. 8B is a table that includes the comparison results of various classifiers.

FIG. 8C is a table that includes overlap values of minimum set of amino acid properties describing disease association.

FIG. 8D is table that includes comparison of values of gene specific algorithms for predicting pathogenicity in other genes.

FIG. 9A summarizes the performance of the PSAAP classifier in classifying RET curated mutations with uncertain outcomes and compares its performance to other methods available in the art.

FIG. 9B is a table that includes the comparison outcome of selected RET mutations using PolyPhen, SIFT, and MutPred.

FIG. 10A illustrates a schematic of the RET protein with clinically curated variants.

FIG. 10B illustrates a schematic of the RET protein with predicted disease association for uncertain variants mapped across protein location.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

Figure 1:
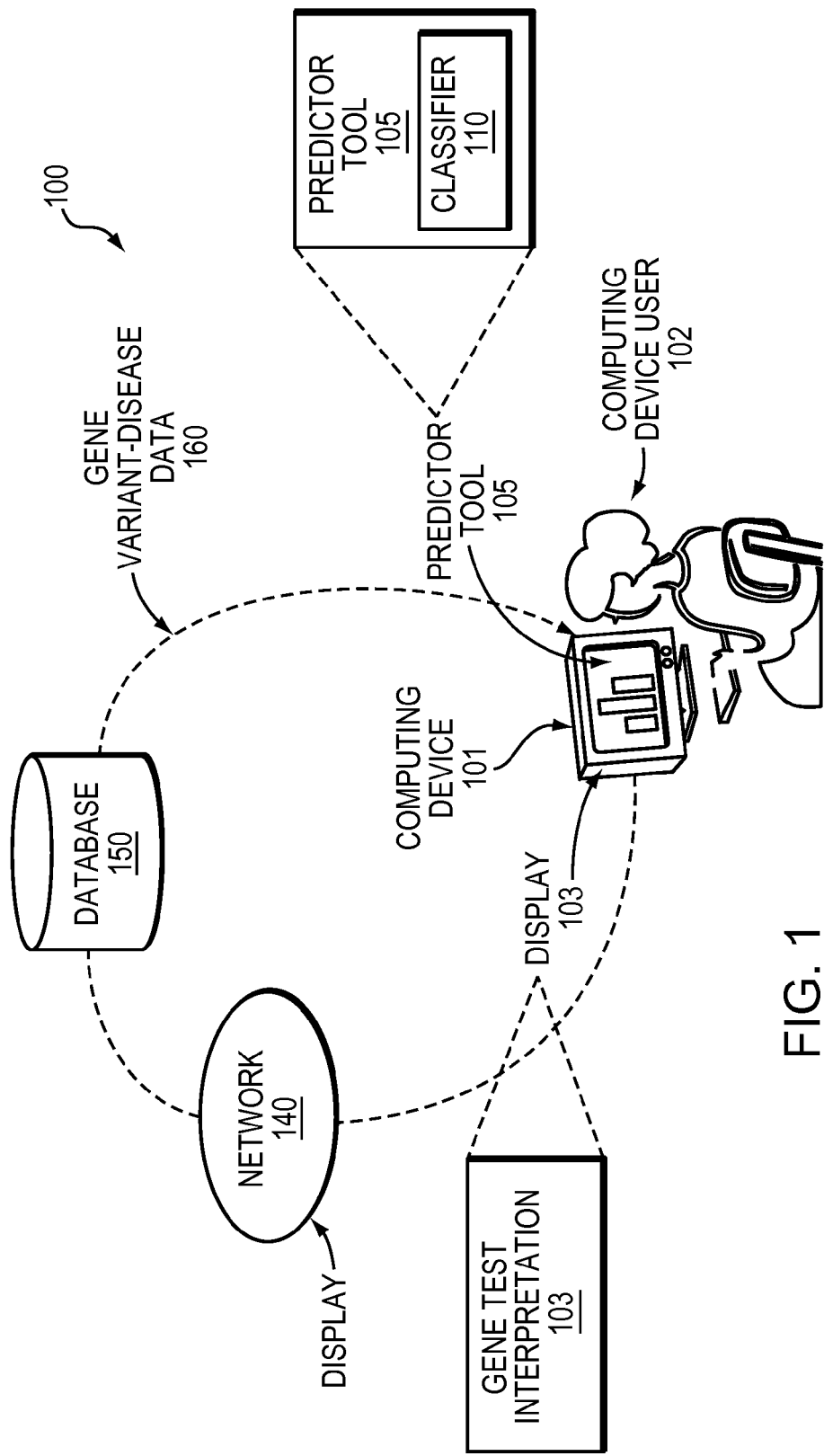
FIG. 1 is a high-level block diagram of an embodiment of the present invention for interpreting a gene test.

FIG. 1 is a high-level block diagram 100 of an embodiment of the present invention for interpreting a gene test. A user 102 of a computing device 101 may access a database 150 to obtain gene variant-disease data 160 from the database 150. The term "gene variant" refers to a specific form of alteration/variation in the normal sequence of a gene. Genetic variations among individuals may occur on different scales, ranging from variations in the number and appearance of the chromosomes to nucleotide. Although the significance of a gene variant or a gene variation is often unclear, in some cases, available studies of genotypes and their corresponding phenotype may be used to determine the significance of a gene variant. The database 150 may store, collect, and/or display information regarding gene variants and their possible disease association (i.e., gene variant-disease data).

The database 150 may be local or remote to the computing device. Although not shown in FIG. 1, in certain embodiments, the user 102 may access more than one database of gene variant-disease data, each of which may be local or remote to the computing device. In some embodiments, the computing device user 102 may access a remote database 150 via a network (e.g., band limited communications network). In some embodiments, the computing device user may submit a request for the gene variant-disease data 160 to the database 150 and receive the data 160 from the database in response to that request.

The computing device 101 may include a machine-implemented predictor tool 105 which may be used to interpret a gene test. The prediction tool 105 may include a classifier 110 that is responsible for performing the procedures required for classifying and interpreting the gene test. The details of the consensus classifier 110 are described later with reference to FIGS. 3-10.

In some embodiments, the interpretation results may be reported to the computing device user 102 on the display 103 of the computing device 101. In certain embodiments, in addition to or in place of displaying the gene test interpretation results, the computing device 101 may employ other reporting schemes known in the art to report the gene test interpretation results.

The term "gene test," as used herein, refers to a test involving examination of deoxyribonucleic acid (DNA) molecules in search for genetic disorders, identifying individuals carrying a copy of a gene that may be responsible for a disease (carrier screening), diagnostic testing, pre-symptomatic testing, etc.

In some embodiments, the database 150 may store information on single nucleotide variant and their disease association. Generally, a "single nucleotide variant" (SNV) or a "single nucleotide polymorphism" (SNP) refers to variations occurring when a single nucleotide in the genome differs between paired chromosomes of an individual or members of a biological species. Further, the term "non-synonymous single nucleotide polymorphism" (nsSNP) may be used to refer to a point mutation or a change in amino acid sequence as compared to a wild type or reference sequence.

Certain nsSNP variants have been shown to be causative of disease. Therefore, investigating the functional effect of SNP has been of interest for many years. Due to the cost, labor, and expertise required for wet-bench molecular evaluation, computational tools have been used to assist in investigating the functional effect SNP. These computational tools often focus on SNP variants in protein coding regions that change one amino acid for another. The severity of a given amino acid sequence change may range from mild to severe, and has been reported to impact various medical areas, including genetic disease susceptibility (e.g., sickle cell anemia), common disease risks (e.g., Alzheimer's disease risk), or drug sensitivities, as seen in Warfarin treatment. Historically, physical and chemical properties of amino acids have been used as a proxy to assess the functional impact of these substitution mutations.

Some early efforts in predicting amino acid substitution effects focused on metrics of estimating the expected evolutionary distance between each possible amino acid pair. For example, Point Accepted Mutation (PAM) matrices have been used to approximate the evolutionary distance and frequency of amino acids for equivalent protein positions in closely related species. Each matrix, in PAM matrices, includes a number of standard amino acids in corresponding rows and columns, such that the value in a given cell represents the probability of having one amino acid substituted for another. Such matrices are commonly referred to as "substitution" matrices.

A substitution matrix may be used to derive a scoring matrix that may be used to assess the similarities between two aligned sequences. The Blocks of Amino Acid Substitution Matrix (BLOSUM) is an example of a substitution matrix that may be used for sequence alignment of proteins. BLOSUM considers highly conserved protein regions and may be used for more distantly related species. Both PAM and BLOSUM employ raw mutation rates to compute a score for each amino acid substitution and calculate the likelihood that the mutation is caused by an evolutionary change (i.e., over time) and not by sheer chance. Further, these substitution matrices assume that substitutions that are consistent with evolutionary trends conserved across many species are less likely to disrupt protein function. Conversely, substitutions that are not consistent with evolution (i.e., non-conserved substitutions) are more likely associated with disease.

Alternative approaches utilizing amino acid properties have considered how physiochemical properties differ with changes in volume, hydrophobicity, net charge, packing density, and solvent accessibility all shown to correlate with predicted functional impact of SNP variants. For example, the Grantham distance method combines the biophysical properties and evolutionary distances between amino acid pairs, in a setting where the significance of the amino acid substitution is quantified in a three-dimensional (3D) space. Specifically, the significance of the amino acid substitution is quantified, as a weighted Euclidean distance, in the three-dimensional space having amino acid side chain composition, polarity and volume as coordinates. The weighted Euclidean distance is modeled to estimate amino acid substitution mutation rates.

Further, some computational algorithms focus on the fact the importance of the evolutionary distance separating a pair of amino acids depends on the position where an amino acid substitution occurs. Specifically, amino acid distribution at equivalent positions in a protein family is functionally or structurally important, where these positions may not tolerate a variety of amino acid changes. These equivalent positions may be found by constructing an alignment from multiple related protein sequences. Thus, amino acid residues in highly conserved alignment may be assumed to be under some purifying evolutionary selection and important for normal protein function. Computational algorithms may be used to quantify this conserved evolutionary selection in protein activity, such as calculating the frequency of the most common amino acid in an alignment column. For example, Shannon entropy may be used to compute the distribution of all amino acids at a specific aligned position. This idea may further be improved by using relative entropy to augment comparing Shannon entropy of a conserved alignment against the Shannon entropy of the amino acid background distribution.

Some mutation prediction computational algorithms and prediction scoring tools for interpreting gene test consider both physicochemical properties of amino acid substitution and evolutionary conservation. Examples of such methods include Sorting Intolerant From Tolerant (SIFT), Position-Specific Independent Counts (PSIC), Align Grantham Variation Grantham Distance (AGVGD), and Multivariate Analysis of Protein Polymorphism (MAPP) score.

The SIFT algorithm may be used to compute a weighted frequency average of which amino acid residue appears in a multiple alignment position, coupled with an estimate of unobserved variant frequencies.

The PSIC profile score method considers the difference of likelihood between reference and variant amino acid at a given aligned position using a position-specific scoring matrix (PSSM).

The AGVGD method is an extension of the original Grantham distance method that may be used in multiple sequence alignments and true simultaneous multiple comparisons. Grantham variation (GV) may be computed by replacing each value-pair of a given amino acid residue component for composition, polarity, and charge with the maximum and minimum value in that alignment position.

The MAPP score constructs a statistical summary of an alignment column by use of phylogenetic tree and tree topology weighting each sequence by branch length.

Furthermore, some computational algorithms consider protein structure-function relationships of amino acid substitution. For example, solvent accessibility of an amino acid may be used as a predictor of functional impact, where substituting various amino acid residues may disrupt the hydrophobic core of a soluble protein. Structural modeling of disease proteins may be used to determine whether a nsSNP variant results in protein backbone strain or leads to over-packing substitutions. A large number of X-ray crystal structures have been determined which often include protein inter-acting partners, and/or small molecule, peptide ligands or inhibitors. The ability to locate a nsSNP variant on a computational protein structure makes it possible to evaluate whether the amino acid substitution occurs in or near a binding or catalytic site or at a domain-domain interface of protein interaction.

Polymorphism Phenotyping (PolyPhen) is an example of an algorithm that takes advantage of structural modeling. Specifically, PolyPhen is an automated tool that may be used to evaluate any possible impact of amino acid substitution on the structure and function of a human protein. PolyPhen uses a Dictionary of Secondary Structure in Proteins (DSSP) to map a given substitution site to known protein 3D structures.

Mutation Prediction (MutPred) is another example of a prediction algorithm that may be used with the embodiments described herein. MutPred generates mutability profiles of amino acid sequences from the corresponding complementary DNA sequences and generates weighted and un-weighted profiles. In the weighted profiles relative mutabilities are multiplied by the likelihood of clinical detection depending on chemical differences.

PMUT is another example of a mutation prediction algorithm. PMUT uses a two layer neural network and is trained using human mutational data. PMUT allows for either prediction of single point amino acidic mutations or scanning of mutational hot spots. Results are obtained by alanine scanning, identifying massive mutations, and genetically accessible mutations.

Although clinicians often rely on patient history, family segregation, literature review and trusted colleagues to stay informed of the phenotypic consequences of a given gene variant found in a gene test, in absence of traditional evidence, well established machine learning or computational tools may be used to predict and access phenotypic consequences of the gene variant. However, established algorithms do not always complete the prediction, and furthermore are not always in agreement with the curated data or each other.

RET (Rearranged During Transformation) proto-oncogene data are an example of the gene-disease data 160 that may be used with embodiments of the present invention. In some embodiments, well-curated gene variant collections, such as RET data, may be used. Further, in some embodiments, physicochemical properties of amino acids in the coded proteins may be utilized to determine mutation severity.

The RET oncogene is located on chromosome 10q11, with 21 exons coding a full length protein of 1,114 amino acids. Conserved functional domains found within the protein include a signal peptide, cadherin repeat domains, transmembrane domain, and protein tyrosine kinase. Mutations in the RET oncogene have been directly associated with Multiple Endocrine Neoplasia type 2 (MEN2), a hereditary thyroid carcinoma syndrome. Although well known mutations often guide patient therapy and surgical options, other RET sequence mutations vary in functional severity. Some mutations may be pathogenic, some may be benign, and some may be of unknown significance. Curated RET oncogene mutations for MEN2 have been reported, many of which have documented phenotype outcomes.

Figure 2:
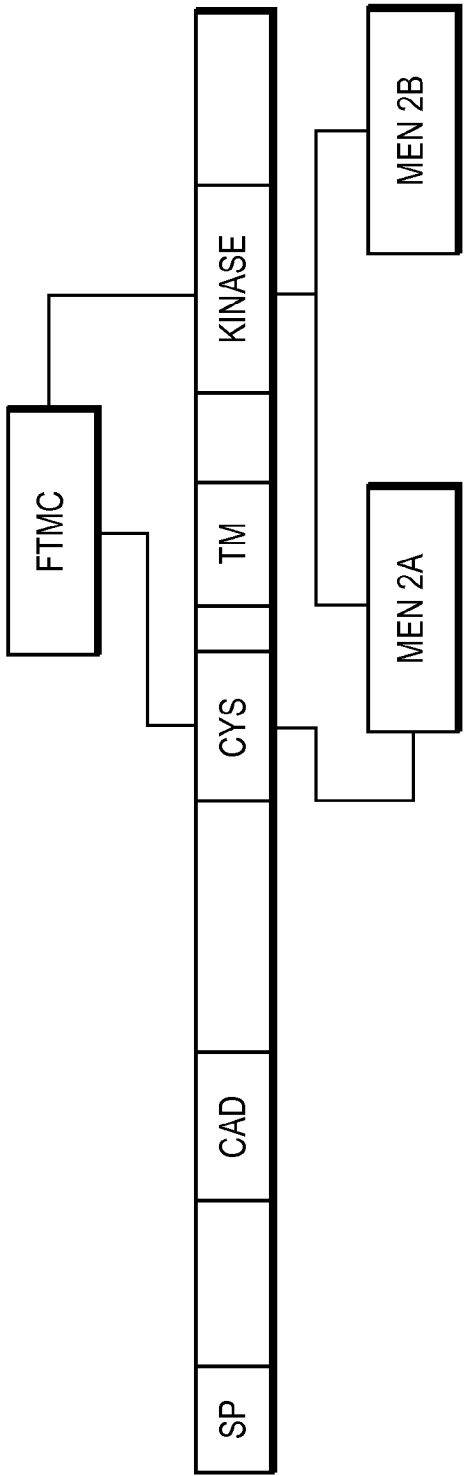
FIG. 2A illustrates RET protein domains and their reported disease causing variants as associated with different MEN2 phenotypes.
FIG. 2B is a table that includes examples of RET mutation guided therapy for surgical removal of thyroid.

FIG. 2A illustrates RET protein domains and their reported disease causing variants as associated with different MEN2 phenotypes. Specifically, conserved domains of signal peptide (SP), cadherin repeat domains (CAD), cysteine rich region (CYS), transmembrane domain (TM), and protein tyrosine kinase (Kinase) are shown. Three specific disease phenotypes have been shown to be associated with these domains. Specifically, familial medullary thyroid cancer (FMTC), multiple endocrine neoplasia type 2A (MEN2A), and multiple endocrine neoplasia type 2B (MEN2B) have been shown to correspond to CYS and Kinase domains.

The RET gene belongs to the cadherin super family and encodes a receptor tyrosine kinase which functions in signaling pathways for cell growth and differentiation. The RET gene plays a critical role in neural crest development and may undergo oncogenic activation, in vivo and in vitro, by cytogenetic rearrangement. The RET gene may further be classified by Gene Ontology (GO) categories of biological process of homophilic cell adhesion, posterior midgut development, and protein amino acid phosphorylation. The GO annotated cellular location of the RET is component integral to membrane and the GO category of molecular functions lists ATP binding, calcium ion binding and transmembrane receptor protein tyrosine kinase activity.

FIG. 2B is a table that includes examples of RET mutation guided therapy for surgical removal of thyroid. The table summarizes mutation-guided therapy for thyroid cancer where surgical removal of thyroid is guided by codon position of the RET mutation.

Figure 3:
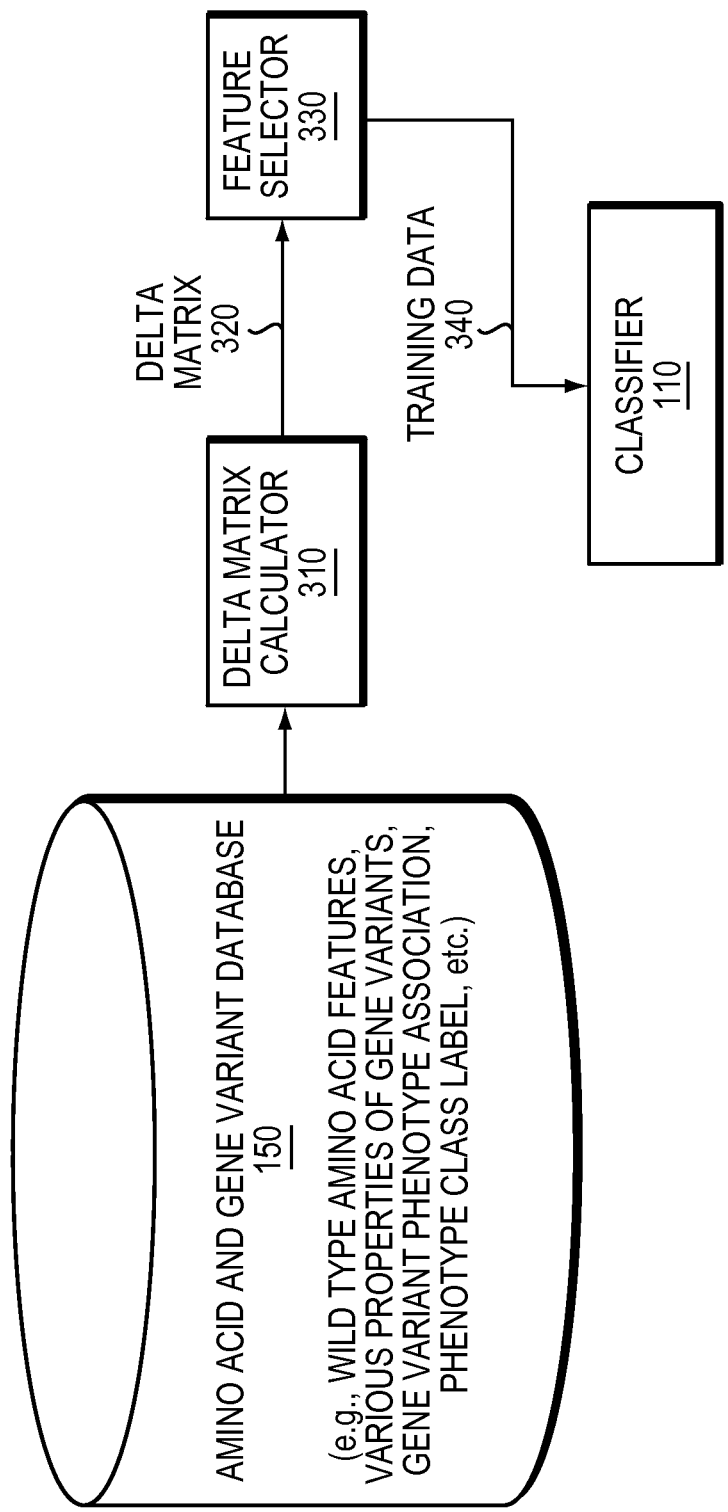
FIG. 3 is a high-level block diagram of a classifier that is being trained according to certain embodiments of the present invention.

FIG. 3 is a high-level block diagram of a classifier 110 that is being trained according to certain embodiments of the present invention. Gene variant data, obtained from a database 150, may be used to train the classifier 110. In certain embodiments, the database 150 may include information concerning wild-type amino acids, wild-type amino acid features, various properties of gene variants, gene variant phenotype association, gene variant phenotype class label (e.g., benign or pathogenic), etc. In some embodiments, RET variant data may be used to train the classifier. For example, in certain embodiments, non-synonymous RET variants may be used to train the classifier. In some embodiments, the Non-synonymous RET variants may be characterized by physicochemical differences in primary amino acid sequence resulting from the mutation. Further, in certain embodiments, attributes of mutation status may be characterized using values corresponding to various amino acid properties. For example, attributes of mutation status may be characterized using physical, chemical, conformational, physiochemical, biochemical, energetic, etc. properties of amino acids.

In some embodiments, a database of numerical indices (not shown), representing various physicochemical and biochemical properties of amino acids and pairs of amino acids, may be obtained. In certain embodiments, the database of numerical indices may include various sections, each of which may be used to represent certain properties of the amino acids. The database of numerical indices may be obtained using any available technique known in the art. For example, in some embodiments, the database of numerical indices may be an amino acid index database (also referred to as an AAindex database). Although, any available database of numerical indices may be used, the term "AAindex database" is used hereinafter to generally refer to the database of numerical indices.

A delta matrix calculator 310 may calculate the absolute value of the difference between each of the amino acid property values included in the AAindex database and corresponding property values in a wild-type amino acid. Accordingly, the outcome of the delta matrix calculator 310 is one or more matrices (delta matrix 320), each of which includes values that correspond to the absolute value of the difference between the value of the property in the amino acid present in the wild type and the one in the mutant (i.e., variant).

A feature selector 330 may be used to select certain properties from the original amino acid attributes in the AAindex matrix. Various feature selection methods known in the art may be used. In certain embodiments, the features may be selected from properties whose differences are reflected in the delta matrix 320. In some embodiments, the difference values included in the delta matrix 320 may be used as classification features.

Training data 340 for use in training the classifier 110 may be formed from the features selected by the feature selector 330. Various methods known in the art may be used to form the training data 340. For example, in one embodiment, k-fold cross validation may be used to access classifier performance.

In k-fold cross validation, the original dataset is partitioned into k samples and of the k samples, k−1 subsamples are used as training data for training the classifier. The cross validation is repeated k times, during which each of the k samples used once. The resulting k outcomes are averaged to produce a single estimation.

In some embodiments, random selection may be used to create the training data 340. In certain embodiments, class labels, such as "pathogenic" and "benign," may be used to describe phenotype severity of the mutations in the training set.

The classifier 110 may use various classification schemes known in the art. For example, classifiers such as Zero Rules (ZeroR), naive Bayesian, Simple Logistic Regression (Simple Logistic), Support Vector Machine (SMO), k-nearest neighbor (IBk), and Random Forest Regression (Random Forest) may be used. In some embodiments, a Naïve Bayesian classifier may be used to perform classification.

Figure 4A:
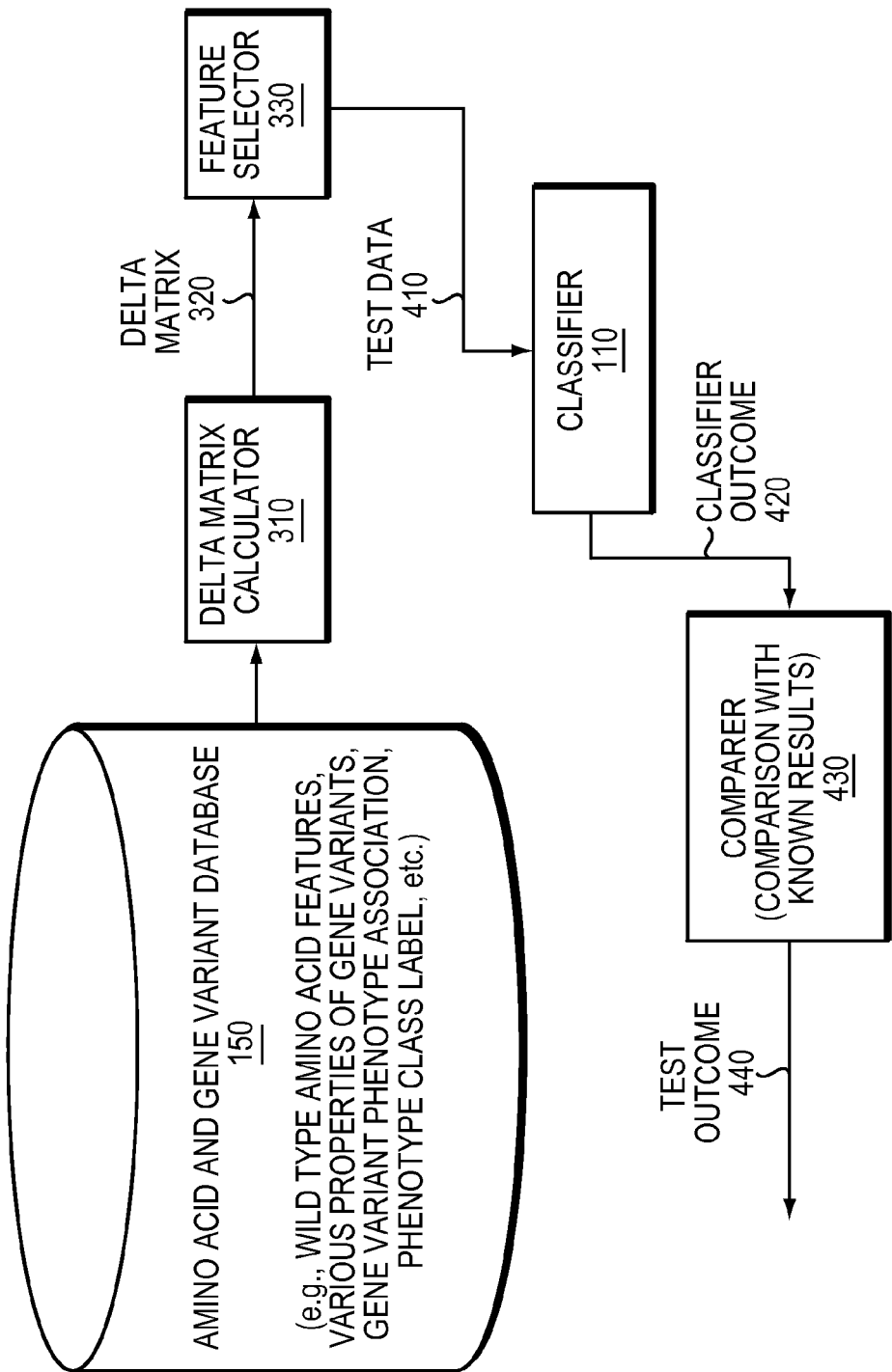
FIG. 4A is a high-level block diagram of a classifier that is being tested according to certain embodiments of the present invention.

FIG. 4A is a high-level block diagram of a classifier 110 that is being tested according to certain embodiments of the present invention. Test data 410 may be prepared in a similar manner as the training data 340 (FIG. 3) was prepared for training the classifier. Specifically, in certain embodiments, random selection may be used to partition the features selected by feature selector 330 into multiple portions (e.g., k portions), some of which (e.g., n portions) may be used for training the classifier 110. The remaining portions (e.g., k−n portions) of the features may be used for testing the classifier 110.

For example, in one embodiment, a clinically curated set (i.e., n=84) of non-synonymous RET mutations with known pathogenicity is used to train and test machine learning classification algorithms. Although training and test sets may include different disease subtypes, such as MEN2A (n=40), MEN2B (n=3), FMTC (n=5), FMTC (n=36), class labels of "pathogenic" and "benign" are used to describe all curated disease association. Random selection is used to build a ⅔ training data 340 set (n=56) and ⅓ test data (shown in FIG. 4A) set (n=28). Attribute selection (i.e., feature selection) is performed during classification training/testing.

In certain embodiments, in an event the classifier 110 produces multiple posterior probabilities of mutation status for a variant's mutation status, the variant's mutation status is assigned according to the highest posterior probability.

In order to investigate the performance of the classifier, a comparer 430 may compare the classifier outcome 420 (i.e., predicted disease associations of the gene variants) to the known outcomes (i.e., known disease associations of the gene variants) and produce a test outcome 440. The test outcome 440 may be indicative of the performance of the classifier.

In some embodiments, the classifier performance may be investigated by calculating the weighted average from a three fold cross validation of sensitivity (i.e., k=3 , true positive rate), specificity (true negative rate), and positive predictive value (precision). Specifically, assuming that the probability of having a true detection (hit) is p, the probability of having a false detection (miss) is $q=1-p$. The probability of having a true positive may be calculated as $p^2$ and the probability of having a false negative may be calculated as pq. Using this definition, the sensitivity of the classifier is $p^2/(p^2+pq)=p$ and the specificity of the classifier is $q^2/(q^2+pq)=q$. The performance of the classifier (i.e., predictive positive value) may be measured as a function of the sensitivity and specificity.

FIG. 4B is an example of a set of genes with clinically curated disease variants that may be used with embodiments described herein. Specifically, the values shown in FIG. 4B, compare the effectiveness of generic gene versus gene specific approaches using a minimum (non-redundant) set of amino acid properties to describe exonic non-synonymous variants coupled with evaluation of overlap and/or trends of biochemical properties of mutation.

Figure 5:
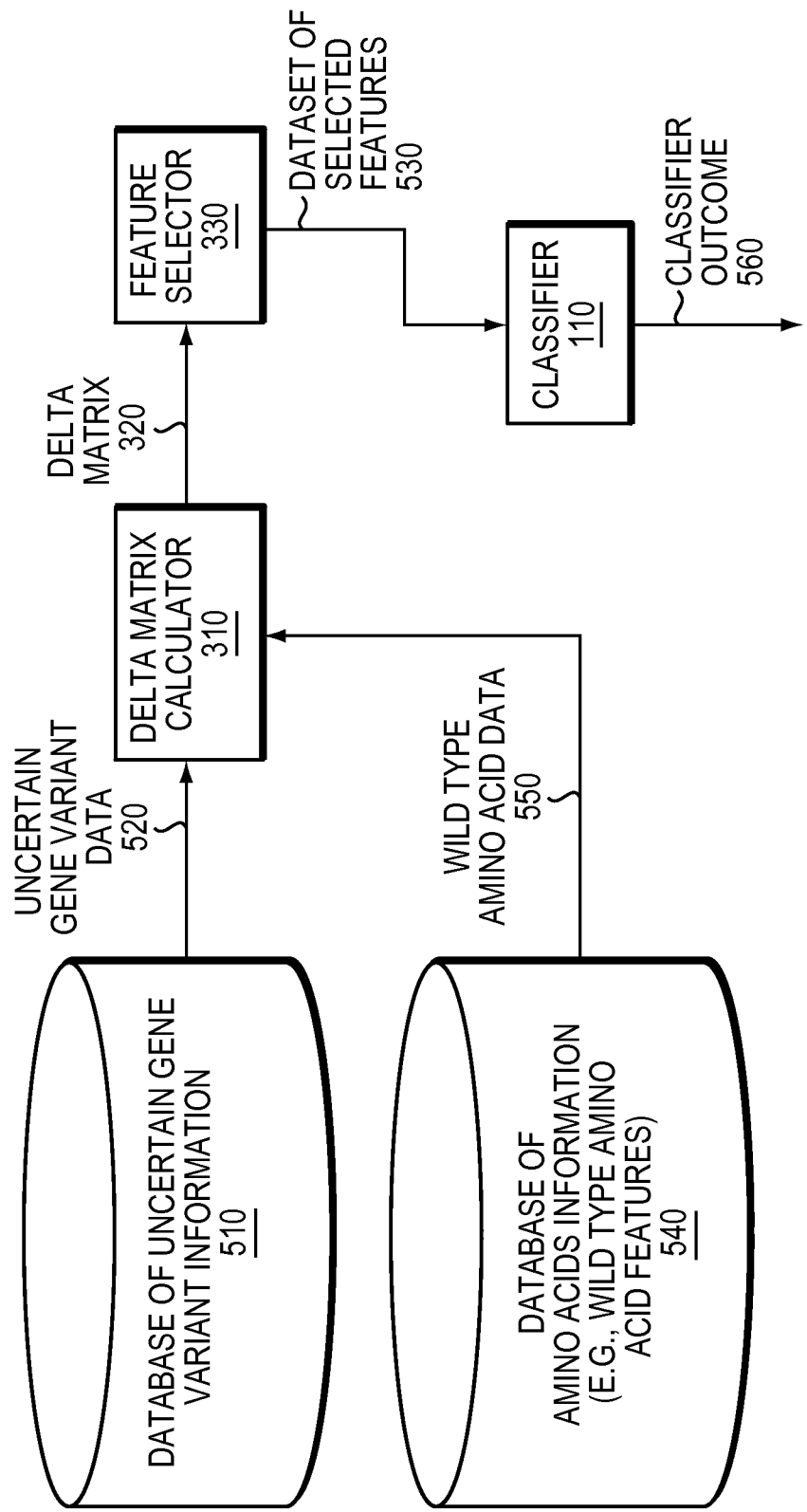
FIG. 5 is a high-level block diagram of a classifier for classifying uncertain gene variants according to certain embodiments disclosed herein.

FIG. 5 is a high-level block diagram of a classifier for classifying uncertain gene variants according to certain embodiments disclosed herein. As shown in FIG. 5, uncertain gene variant data 520, including information regarding uncertain gene variants, may be obtained from a database 510. Such data may include data obtained from a gene test. Similarly, data 550 including information regarding wild type amino acids may be obtained from a database 540 that stores features of wild type amino acids. The delta matrix calculator 310 calculates the difference between the certain properties of the gene variants and their corresponding wild type amino acids. In certain embodiments, the delta matrix calculator 310 may calculate the absolute value of the difference between the features of the gene variants and their corresponding wild type amino acids. The calculated differences may be output from the delta matrix calculator 310 in the form of a matrix (delta matrix 320).

In certain embodiments, the Correlation-based Feature Subset Selection algorithm, together with the Best First (e.g., greedy hill-climbing) search method, may be used to identify the subset of properties that best differentiated benign mutations from pathogenic ones, based on the amino acid changes in RET.

Feature selector 330 may select one or more features for classification from the values stored in the delta matrix 320. The dataset of selected features 530 is forwarded to the classifier 110, which has been already trained using the dataset of known RET gene variants. The classifier processes the dataset 530 and generates a classifier outcome 560 that may be used in interpreting gene test results having uncertain variants.

Figure 6:
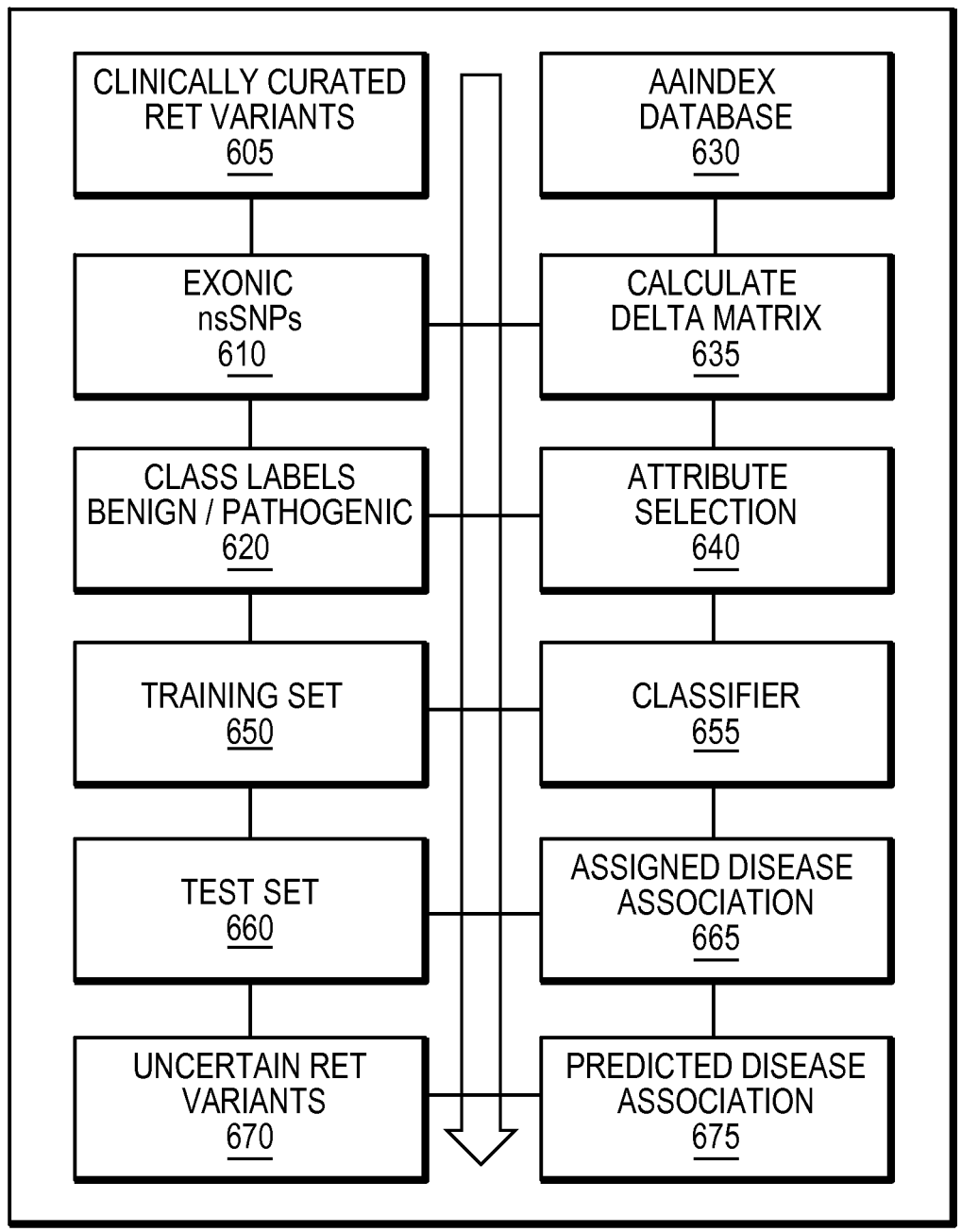
FIG. 6 is a flow diagram of the procedures for interpreting gene test results using a classifier according to certain embodiments described herein.

FIG. 6 is a flow diagram of the procedures for interpreting gene test results using a classifier according to certain embodiments described herein. As noted previously, RET variant data may be used to test and train the classifier 110. In some embodiments, non-synonymous RET variant data may be used 605. Non-synonymous RET variants 605 are characterized by physicochemical differences in primary amino acid sequence resulting from the mutation. The RET variant data may include exonic nsSNP variants 610 with known outcomes of benign and pathogenic 620.

Attribute selection (feature selection) 640 may be performed to select a subset of relevant features that may be used for classification. Specifically, attributes of mutation status may be characterized using values of physical, chemical, conformational, or energetic properties of the genes. In some embodiments, attribute selection may select the difference in the value of certain properties (e.g., chemical or energetic properties) of the gene variants and their corresponding properties in wild type amino acids as classification attributes. In some embodiments, absolute values of the differences may be considered. The properties used in attribute selection 340 may be obtained from an AAindex database 630. As explained above, the AAindex 630 includes a database of numerical indices that represents various physicochemical and biochemical properties of amino acids and pairs of amino acids. For example, in one embodiment, k-fold cross validation may be utilized to choose a number of amino acid attributes included in an AAindex. Examples of such attributes include alpha NH chemical shifts, normalized frequency of C terminal helix, normalized frequency of chain reversal R, normalized positional frequency at helix termini N2 , partition coefficient Garel, relative preference value at C2 , relative preference value at N1 , weights for beta sheet at the window position of 0 , amino acid distribution, average relative fractional occurrence in A0(i), average relative probability of inner beta sheet, composition, effective partition energy, free energy in alpha helical region, frequency of the third residue in turn, helix formation parameters (delta delta G), hydrophobicity, membrane buried preference parameters, normalized frequency of beta structure, normalized frequency of coil, normalized positional frequency at helix termini Cc, STERIMOL maximum width of the side chain, or Zimm Bragg parameter sigmax1.0E4. The above listing of attributes is not an exhaustive list of attributes. Any attributes known in the art may be used with the embodiments described herein.

In certain embodiments, the AAindex may include at least one of the following amino acid attributes: alpha-CH chemical shifts, hydrophobicity index, signal sequence helical potential, membrane-buried preference parameters, conformational parameter of inner helix, conformational parameter of beta-structure, conformational parameter of beta-turn, average flexibility indices, residue volume, information value for accessibility; average fraction 35%, information value for accessibility; average fraction 23%, retention coefficient in TFA, retention coefficient in HFBA, transfer free energy to surface, apparent partial specific volume, alpha-NH chemical shifts, alpha-CH chemical shifts, spin-spin coupling constants 3JHalpha-NH, normalized frequency of alpha-helix, normalized frequency of extended structure, steric parameter, polarizability parameter, free energy of solution in water kcal/mole, the Chou-Fasman parameter of the coil conformation, a parameter defined from the residuals obtained from the best correlation of the Chou-Fasman parameter of beta-sheet, the number of atoms in the side chain labeled 1+1 , the number of atoms in the side chain labelled 2+1 , the number of atoms in the side chain labeled 3+1 , the number of bonds in the longest chain, a parameter of charge transfer capability, a parameter of charge transfer donor capability, average volume of buried residue, residue accessible surface area in tripeptide, residue accessible surface area in folded protein, proportion of residues 95% buried, 0 proportion of residues 100% buried, normalized frequency of beta-turn, normalized frequency of alpha-helix, normalized frequency of beta-sheet, normalized frequency of beta-turn, normalized frequency of N-terminal helix, normalized frequency of C-terminal helix, normalized frequency of N-terminal non helical region, normalized frequency of C-terminal non helical region, normalized frequency of N-terminal beta-sheet, normalized frequency of C-terminal beta-sheet, normalized frequency of N-terminal non beta region, normalized frequency of C-terminal non beta region, frequency of the 1st residue in turn, frequency of the 2nd residue in turn, frequency of the 3rd residue in turn, frequency of the 4th residue in turn, normalized frequency of the 2nd and 3rd residues in turn, normalized hydrophobicity scales for alpha-proteins, normalized hydrophobicity scales for beta-proteins, normalized hydrophobicity scales for alpha+beta-proteins, normalized hydrophobicity scales for alpha/beta-proteins, normalized average hydrophobicity scales, partial specific volume, normalized frequency of middle helix, normalized frequency of beta-sheet, normalized frequency of turn, size, amino acid composition, relative mutability, membrane preference for cytochrome b: MPH89, average membrane preference: AMP07, consensus normalized hydrophobicity scale, solvation free energy, atom-based hydrophobic moment, direction of hydrophobic moment, molecular weight, melting point, optical rotation, pK—N, K—C, hydrophobic parameter pi, graph shape index, smoothed upsilon steric parameter, normalized van der Waals volume, STERIMOL length of the side chain, STERIMOL minimum width of the side chain, STERIMOL maximum width of the side chain, N.m.r. chemical shift of alpha-carbon, localized electrical effect, number of hydrogen bond donors, number of full nonbonding orbitals, positive charge, negative charge, pK-a(RCOOH), helix-coil equilibrium constant, helix initiation parameter at position i−1, helix initiation parameter at position i i+1 j−1, helix termination parameter at position j+1, partition coefficient, alpha-helix indices, alpha-helix indices for alpha-proteins, alpha-helix indices for beta-proteins, alpha-helix indices for alpha/beta-proteins, beta-strand indices, beta-strand indices for beta-proteins, beta-strand indices for alpha/beta-proteins, aperiodic indices, aperiodic indices for alpha-proteins, aperiodic indices for beta-proteins, aperiodic indices for alpha/beta-proteins, hydrophobicity factor, residue volume, composition, polarity, volume, partition energy, hydration number, hydrophilicity value, heat capacity, absolute entropy, entropy of formation, normalized relative frequency of alpha-helix, normalized relative frequency of extended structure, normalized relative frequency of bend, normalized relative frequency of bend R, normalized relative frequency of bend S, normalized relative frequency of helix end, normalized relative frequency of double bend, normalized relative frequency of coil, average accessible surface area, percentage of buried residues, percentage of exposed residues, ratio of buried and accessible molar fractions, transfer free energy, hydrophobicity, pK (—COOH), relative frequency of occurrence, relative mutability, amino acid distribution, sequence frequency, average relative probability of helix, average relative probability of beta-sheet, average relative probability of inner helix, average relative probability of inner beta-sheet, flexibility parameter for no rigid neighbors, flexibility parameter for one rigid neighbor, flexibility parameter for two rigid neighbors, the Kerr-constant increments, net charge, side chain interaction parameter, side chain interaction parameter, fraction of site occupied by water, side chain volume, hydropathy index, transfer free energy CHP/water, hydrophobic parameter, distance between C-alpha and centroid of side chain, side chain angle theta(AAR), side chain torsion angle phi(AAAR), radius of gyration of side chain, van der Waals parameter R0, van der Waals parameter epsilon, normalized frequency of alpha-helix with weights, normalized frequency of beta-sheet with weights, normalized frequency of reverse turn with weights, normalized frequency of alpha-helix unweighted, normalized frequency of beta-sheet unweighted, normalized frequency of reverse turn unweighted, frequency of occurrence in beta-bends, conformational preference for all beta-strands, conformational preference for parallel beta-strands, conformational preference for antiparallel beta-strands, average surrounding hydrophobicity, normalized frequency of alpha-helix, normalized frequency of extended structure, normalized frequency of zeta R, normalized frequency of left-handed alpha-helix, normalized frequency of zeta L, normalized frequency of alpha region, refractivity, retention coefficient in HPLC pH 7.4, retention coefficient in HPLC pH 2.1, retention coefficient in NaClO4, retention coefficient in NaH2PO4, average reduced distance for C-alpha, average reduced distance for side chain, average side chain orientation angle, effective partition energy, normalized frequency of alpha-helix, normalized frequency of beta-structure, normalized frequency of coil, AA composition of total proteins, SD of AA composition of total proteins, AA composition of mt-proteins, normalized composition of mt-proteins, AA composition of mt-proteins from animal, normalized composition from animal, AA composition of mt-proteins from fungi and plant, normalized composition from fungi and plant, AA composition of membrane proteins, normalized composition of membrane proteins, transmembrane regions of non-mt-proteins, transmembrane regions of mt-proteins, ratio of average and computed composition, AA composition of CYT of single-spanning proteins, AA composition of CYT2 of single-spanning proteins, AA composition of EXT of single-spanning proteins, AA composition of EXT2 of single-spanning proteins, A composition of MEM of single-spanning proteins, AA composition of CYT of multi-spanning proteins, AA composition of EXT of multi-spanning proteins, AA composition of MEM of multi-spanning proteins, a contact number, a contact number, transfer energy organic solvent/water, average non-bonded energy per atom, short and medium range non-bonded energy per atom, long range non-bonded energy per atom, average non-bonded energy per residue, short and medium range non-bonded energy per residue, optimized beta-structure-coil equilibrium constant, optimized propensity to form reverse turn, optimized transfer energy parameter, optimized average non-bonded energy per atom, optimized side chain interaction parameter, normalized frequency of alpha-helix from LG, normalized frequency of alpha-helix from CF, normalized frequency of beta-sheet from LG, normalized frequency of beta-sheet from CF, normalized frequency of turn from LG, normalized frequency of turn from CF, normalized frequency of alpha-helix in all-alpha class, normalized frequency of alpha-helix in alpha+beta class, normalized frequency of alpha-helix in alpha/beta class, normalized frequency of beta-sheet in all-beta class, normalized frequency of beta-sheet in alpha+beta class, normalized frequency of beta-sheet in alpha/beta class, normalized frequency of turn in all-alpha class, normalized frequency of turn in all-beta class, normalized frequency of turn in alpha+beta class, normalized frequency of turn in alpha/beta class, HPLC parameter, nartition coefficient, surrounding hydrophobicity in folded form, average gain in surrounding hydrophobicity, average gain ratio in surrounding hydrophobicity, surrounding hydrophobicity in alpha-helix, surrounding hydrophobicity in beta-sheet, surrounding hydrophobicity in turn, accessibility reduction ratio, average number of surrounding residues, intercept in regression analysis, slope in regression analysis×1.0E1, correlation coefficient in regression analysis, hydrophobicity, relative frequency in alpha-helix, relative frequency in beta-sheet, relative frequency in reverse-turn, helix-coil equilibrium constant, beta-coil equilibrium constant, weights for alpha-helix at the window position of −6, weights for alpha-helix at the window position of −5, weights for alpha-helix at the window position of −4, weights for alpha-helix at the window position of −3, weights for alpha-helix at the window position of −2, weights for alpha-helix at the window position of −1, weights for alpha-helix at the window position of 0, weights for alpha-helix at the window position of 1, weights for alpha-helix at the window position of 2, weights for alpha-helix at the window position of 3, weights for alpha-helix at the window position of 4, weights for alpha-helix at the window position of 5, weights for alpha-helix at the window position of 6, weights for beta-sheet at the window position of −6 , weights for beta-sheet at the window position of −5 , weights for beta-sheet at the window position of −4 , weights for beta-sheet at the window position of −3 , weights for beta-sheet at the window position of −2, weights for beta-sheet at the window position of −1 , weights for beta-sheet at the window position of 0 , weights for beta-sheet at the window position of 1 , weights for beta-sheet at the window position of 2 , weights for beta-sheet at the window position of 3 , weights for beta-sheet at the window position of 4 , weights for beta-sheet at the window position of 5 , weights for beta-sheet at the window position of 6 , weights for coil at the window position of −6 , weights for coil at the window position of −5 , weights for coil at the window position of −4 , weights for coil at the window position of −3 , weights for coil at the window position of −2 , weights for coil at the window position of −1 , weights for coil at the window position of 0 , weights for coil at the window position of 1 , weights for coil at the window position of 2 , weights for coil at the window position of 3 , weights for coil at the window position of 4 , weights for coil at the window position of 5 , weights for coil at the window position of 6 , average reduced distance for C-alpha, average reduced distance for side chain, side chain orientational preference, average relative fractional occurrence in A0(i), average relative fractional occurrence in AR(i), average relative fractional occurrence in AL(i), average relative fractional occurrence in EL(i), average relative fractional occurrence in E0(i), average relative fractional occurrence in ER(i), average relative fractional occurrence in A0(i−1), average relative fractional occurrence in AR(i−1), average relative fractional occurrence in AL(i−1), average relative fractional occurrence in EL(i−1), average relative fractional occurrence in E0(i−1), average relative fractional occurrence in ER(i−1), value of theta(i), value of theta(i−1), transfer free energy from chx to wat, transfer free energy from oct to wat, transfer free energy from vap to chx, transfer free energy from chx to oct, transfer free energy from vap to oct, accessible surface area, energy transfer from out to in (95% buried), mean polarity, relative preference value at N", Relative preference value at N', relative preference value at N-cap, relative preference value at N1 , relative preference value at N2 , relative preference value at N3 , relative preference value at N4 , relative preference value at N5 , relative preference value at Mid, relative preference value at C5 , relative preference value at C4 , relative preference value at C3 , relative preference value at C2 , relative preference value at C1 , relative preference value at C-cap, relative preference value at C', relative preference value at C", information measure for alpha-helix, information measure for N-terminal helix, information measure for middle helix, information measure for C-terminal helix, information measure for extended, information measure for pleated-sheet, information measure for extended without H-bond, information measure for turn, information measure for N-terminal turn, information measure for middle turn, information measure for C-terminal turn, information measure for coil, information measure for loop, hydration free energy, mean area buried on transfer, mean fractional area loss, side chain hydropathy uncorrected for solvation, side chain corrected for solvation hydropathy, loss of Side chain hydropathy by helix formation, transfer free energy, principal component I, principal component II, principal component III, principal component IV, Zimm-Bragg parameter s at 20 C., Zimm-Bragg parameter sigma× 1.0E4 , Optimal matching hydrophobicity, normalized frequency of alpha-helix, normalized frequency of isolated helix, normalized frequency of extended structure, normalized frequency of chain reversal R, normalized frequency of chain reversal S, normalized frequency of chain reversal D, normalized frequency of left-handed helix, normalized frequency of zeta R, normalized frequency of coil, normalized frequency of chain reversal, relative population of conformational state A, relative population of conformational state C, relative population of conformational state E, electron-ion interaction potential, bitterness, transfer free energy to lipophilic phase, average interactions per side chain atom, RF value in high salt chromatography, propensity to be buried inside, free energy change of epsilon(i) to epsilon(ex), free energy change of alpha(Ri) to alpha(Rh), free energy change of epsilon(i) to alpha(Rh), polar requirement, hydration potential, principal property value z1 , principal property value z2 , principal property value z3 , unfolding Gibbs energy in water pH 7.0 , unfolding Gibbs energy in water pH 9.0 , activation Gibbs energy of unfolding pH 7.0 , activation Gibbs energy of unfolding pH9.0 , dependence of partition coefficient on ionic strength, hydrophobicity, bulkiness, polarity, isoelectric point, RF rank, normalized positional residue frequency at helix termini N4', normalized positional residue frequency at helix termini N''', normalized positional residue frequency at helix termini N'', normalized positional residue frequency at helix termini N', normalized positional residue frequency at helix termini Nc, normalized positional residue frequency at helix termini N1, normalized positional residue frequency at helix termini N2 , normalized positional residue frequency at helix termini N3 , normalized positional residue frequency at helix termini N4, normalized positional residue frequency at helix termini N5 , normalized positional residue frequency at helix termini C5 , normalized positional residue frequency at helix termini C4, normalized positional residue frequency at helix termini C3 , normalized positional residue frequency at helix termini C2 , normalized positional residue frequency at helix termini C1, normalized positional residue frequency at helix termini Cc, normalized positional residue frequency at helix termini C', normalized positional residue frequency at helix termini C", normalized positional residue frequency at helix termini C''', normalized positional residue frequency at helix termini C4', delta G values for the peptides extrapolated to 0 M urea, helix formation parameters (delta delta G), normalized flexibility parameters (B-values) average, normalized flexibility parameters (B-values) for each residue surrounded by none rigid neighbours, normalized flexibility parameters (B-values) for each residue surrounded by one rigid neighbours, normalized flexibility parameters (B-values) for each residue surrounded by two rigid neighbours, free energy in alpha-helical conformation, free energy in alpha-helical region, free energy in beta-strand conformation, free energy in beta-strand region, free energy in beta-strand region, free energies of transfer of AcW1-X-LL peptides from bilayer interface to water, thermodynamic beta sheet propensity, turn propensity scale for transmembrane helices, alpha helix propensity of position 44 in T4 lysozyme, p-Values of mesophilic proteins based on the distributions of B values, p-Values of thermophilic proteins based on the distributions of B values, distribution of amino acid residues in the 18 non-redundant families of thermophilic proteins, distribution of amino acid residues in the 18 non-redundant families of mesophilic proteins, distribution of amino acid residues in the alpha-helices in thermophilic protein, distribution of amino acid residues in the alpha-helices in mesophilic proteins, side-chain contribution to protein stability (kJ/mol), propensity of amino acids within pi-helices, hydropathy scale based on self-information values in the two-state model (5% accessibility), hydropathy scale based on self-information values in the two-state model (9% accessibility), hydropathy scale based on self-information values in the two-state model (16% accessibility), hydropathy scale based on self-information values in the two-state model (20% accessibility), hydropathy scale based on self-information values in the two-state model (25% accessibility), hydropathy scale based on self-information values in the two-state model (36% accessibility), hydropathy scale based on self-information values in the two-state model (50% accessibility), averaged turn propensities in a transmembrane helix, alpha-helix propensity derived from designed sequences, beta-sheet propensity derived from designed sequences, composition of amino acids in extracellular proteins (percent), composition of amino acids in anchored proteins (percent), composition of amino acids in membrane proteins (percent), composition of amino acids in intracellular proteins (percent), composition of amino acids in nuclear proteins (percent), surface composition of amino acids in intracellular proteins of thermophiles (percent), surface composition of amino acids in intracellular proteins of mesophiles (percent), surface composition of amino acids in extracellular proteins of mesophiles (percent), surface composition of amino acids in nuclear proteins (percent), interior composition of amino acids in intracellular proteins of thermophiles (percent), interior composition of amino acids in intracellular proteins of mesophiles (percent), interior composition of amino acids in extracellular proteins of mesophiles (percent), interior composition of amino acids in nuclear proteins (percent), entire chain composition of amino acids in intracellular proteins of thermophiles (percent), entire chain composition of amino acids in intracellular proteins of mesophiles (percent), entire chain composition of amino acids in extracellular proteins of mesophiles (percent), entire chain composition of amino acids in nuclear proteins (percent), screening coefficients gamma local, screening coefficients gamma non-local, slopes tripeptide FDPB VFF neutral, slopes tripeptides LD VFF neutral, slopes tripeptide FDPB VFF noside, slopes tripeptide FDPB VFF all, slopes tripeptide FDPB PARSE neutral, slopes dekapeptide FDPB VFF neutral, slopes proteins FDPB VFF neutral, side-chain conformation by gaussian evolutionary method, amphiphilicity index, volumes including the crystallographic waters using the ProtOr, volumes not including the crystallographic waters using the ProtOr, electron-ion interaction potential values, hydrophobicity scales, hydrophobicity coefficient in RP-HPLC C18 with 0.1% TFA/MeCN/H2O, hydrophobicity coefficient in RP-HPLC C8 with 0.1%TFA/MeCN/H2O, hydrophobicity coefficient in RP-HPLC C4 with 0.1% TFA/MeCN/H2O, hydrophobicity coefficient in RP-HPLC C18 with 0.1% TFA/2-PrOH/MeCN/H2O, hydrophilicity scale, retention coefficient at pH 2, modified Kyte-Doolittle hydrophobicity scale, interactivity scale obtained from the contact matrix, interactivity scale obtained by maximizing the mean of correlation coefficient over single-domain globular proteins, interactivity scale obtained by maximizing the mean of correlation coefficient over pairs of sequences sharing the TIM barrel fold, linker propensity index, knowledge-based membrane-propensity scale from 1D_Helix in MPtopo databases, knowledge-based membrane-propensity scale from 3D_Helix in MPtopo databases, linker propensity from all dataset, linker propensity from 1-linker dataset, linker propensity from 2-linker dataset, linker propensity from 3-linker dataset, linker propensity from small dataset (linker length is less than six residues), linker propensity from medium dataset (linker length is between six and 14 residues), linker propensity from long dataset (linker length is greater than 14 residues), linker propensity from helical (annotated by DSSP) dataset, linker propensity from non-helical (annotated by DSSP) dataset, the stability scale from the knowledge-based atom-atom potential, the relative stability scale extracted from mutation experiments, buriability, linker index, mean volumes of residues buried in protein interiors, average volumes of residues, hydrostatic pressure asymmetry index PAI, hydrophobicity index, Average internal preferences, hydrophobicity-related index, apparent partition energies calculated from Wertz-Scheraga index, apparent partition energies calculated from Robson-Osguthorpe index, apparent partition energies calculated from Janin index, apparent partition energies calculated from Chothia index, hydropathies of amino acid side chains neutral form, hydropathies of amino acid side chains pi-values in pH 7.0, weights from the IFH scale, hydrophobicity index 3.0 pH, scaled side chain hydrophobicity values, hydrophobicity scale from native protein structures, NNEIG index, SWEIG index, PRIFT index, PRILS index, ALTFT index, ALTLS index, TOTFT index, TOTLS index, relative partition energies derived by the Bethe approximation, optimized relative partition energies—method A, optimized relative partition energies—method B, optimized relative partition energies—method C, optimized relative partition energies—method D, hydrophobicity index, or hydrophobicity index.

For each RET variant, matrices of delta values 635 for each biochemical property of the substituted amino acid are calculated using the corresponding AAindex 630. The resulting mutation are described by an array of variables, archived using a structured query language (SQL), that corresponds to the absolute value of the difference between the value of the property in the amino acid present in the wild type and the one in the mutant. Attribute selection (feature selection) 640 may be performed during classification training/testing.

A training dataset 650 and a test dataset 660 may be selected from the values in the delta matrix. For example, in some embodiments, random selection may be used to build the training set 650 and the test set 660. Although training and test sets may include different disease subtypes, such as MEN2A, MEN2B, FMTC, FMTC, class labels of "pathogenic" and "benign" are used to describe all curated disease association.

A classifier, such as a naive Bayesian classifier 655, may be employed to classify the variants. Specifically, the training set 650 may be used to train the classifier 655. The test set 660 is then tested using the classifier 655 and the outcome of the test is used to assign disease association 665 to the gene variants in the test set 660.

Upon completion of training, uncertain variants 670 may also be analyzed. The predicted disease associations of the uncertain variants 675 may be output from the classifier 110.

The performance of the classifier 110 may be evaluated using calculated values of sensitivity (true positive rate), specificity (true negative rate), and positive predictive value (precision).

FIG. 7 is a table that summarizes performance of various classifiers (e.g., mutation prediction tools and traditional classifiers), including a Primary Sequence Amino Acid Properties (PSAAP) classifier 110 developed according to certain embodiments described herein, in interpreting gene test results using a dataset of RET gene variant-disease data. The classifier performance is ranked by positive predictive value (PPV) or the percentage of variants classified as pathogenic that actually were pathogenic.

For the dataset used, the ZeroR classifier (zero rules), which selects the majority class by default, yields a baseline performance of 55.7%. The nearest neighbor, random forest, support vector machine, and simple logistic give similar performance to each other with 77.6%, 78.9%, 79.1%, and 81.4% respectively. The naïve Bayesian classifier appears to be the best performing algorithm with a positive predictive value of 82.7%, which translates to a gain in performance of 27% over the ZeroR classifier. Further, as shown, the traditional classifiers (e.g., ZeroR, IBk, Random Forest, SMO, Simple Logistic, Naïve Bayesian) perform better than or similar to the existing mutation prediction algorithms (e.g., PolyPhen, SIFT, MutPred, and PMUT). Specifically, the PolyPhen, SIFT, MutPred, and PMUT result in positive predictive values of 54.1%, 77.9%, 84.3%, and 72.3%, respectively. The PSAAP classifier 110, which was developed according to certain embodiments described herein and uses a Naïve Bayesian classier, yields the highest performance at 8.3%.

FIG. 8A summarizes the performance of the PSAAP classifier, in classifying RET curated mutations with known outcomes, and compares its performance to other methods available in the art. Specifically, an independent test set of RET curated mutations with known outcomes is used to evaluate performance of different categories of classifier algorithms. The PSAAP algorithm according to the embodiments described herein, which uses a Bayesian classifier, yields a sensitivity of 0.938, specificity of 0.867 and positive predictive value (precision) of 0.883. A benchmark of prediction performance for the established algorithms (MutPred, PolyPhen, PMut, and SIFT) is also performed using the same dataset. Following the 88% (i.e., 0.883 precision) of the PSAAP classifier, MutPred is next closest to predicting the correct disease outcomes for the known RET variants with 84% precision. PolyPhen yields the highest specificity for RET variant disease association of 92%, yet has the lowest precision at 54%. The PMut correctly predicts gene variant disease outcomes with 72% precision but has the lowest specificity at 59%. The MutPred, PolyPhen, PMut, and SIFT algorithms are evaluated using their default settings.

FIG. 8B is a table that includes the PPV results of the PSAAP algorithm, gene specific and all-gene algorithms as compared to other available algorithms. As shown in FIG. 8B, a majority of genes (13 out of 15) analyzed using the gene-specific PSAAP trained algorithm have improved PPV as compared to other algorithms, with the overall PPV increasing 8.8% to 22.0%. For example, the PSAAP model specific for SPRED1, when analyzed using established prediction algorithms yields precision scores from 56% to 71%. As mentioned above, the PSAAP model outperforms established algorithms, where on-line predictions for ACVRL1 only ranged from 57% to 81% PPV. Two exceptions to this trend are GALT and SMAD, in which MutPred and/or PMut scored slightly higher.

FIG. 8C is a table that includes overlap values of minimum set of amino acid properties describing disease association. A minimum attribute set of amino acid properties appears to be specific to each gene-disease, with overlap found among different genes using three feature selection methods ranging from 11% to 80%. Representative examples are shown in FIG. 8C. The gene models with more shared amino acid attributes (GALT, 80%; NF1, 62%; SPRED1, 60%) also have the best generalizability. Of note, both SMAD4 and GALT do well using the established on-line prediction tools, where SMAD4 also had 58% overlap. Without considering the above mentioned 4 genes, the overlap ranged from only 11% to 37%. Overlap for the all gene data set follows this same trend, showing only 38% overlap between the feature selection methods.

FIG. 8D is table that includes comparison of values of gene specific algorithms for predicting pathogenicity in other genes. For the genes studied here, the PSAAP gene-specific prediction performs well. FIG. 8D displays the PPV values. The self against self is plotted on the diagonal in blue with ppv>80 bolded. Other gene predictor performance with PPV above 80 is shaded in orange. Interestingly, gene-specific prediction models do not seem to generalize well—even across similar protein functional families. For instance, FIG. 8D shows that the RET kinase trained model (94% PPV) performed lower for the ACVRL1 kinase (84% PPV) while the ACVRL1 trained predictor (88% PPV) only predicted RET with 80% PPV. Additionally, the carboxylase enzyme BTD (91% PPV) only predicted the hydroxylase PAH gene variant outcome with 76% PPV, while the PAH trained predictor (89% PPV) only predicted BTD with 59% PPV. It is notable however, that 3 out of 15 genes (SPRED1, NF1 and GALT) yielded comparable numbers for predicting disease association across other genes.

Figure 8E:
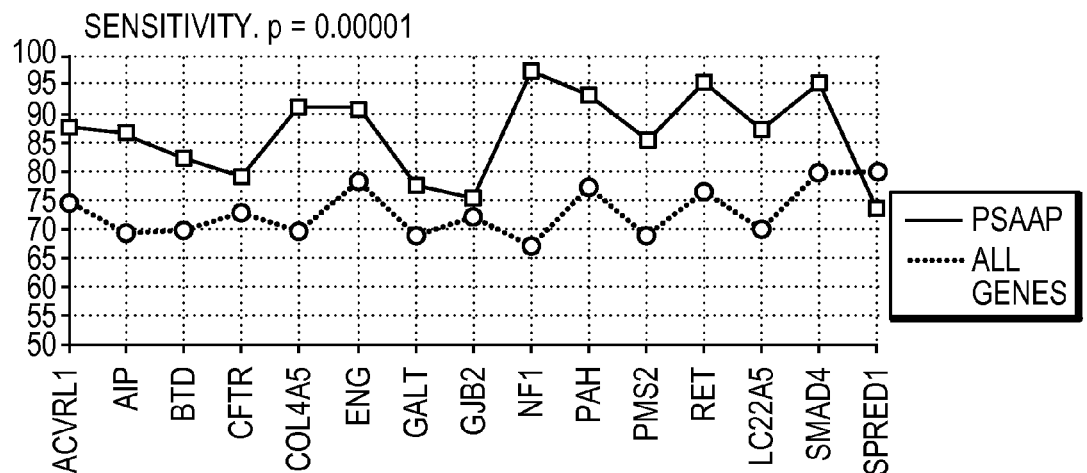
FIGS. 8E, 8F, 8G illustrate the performance of the gene-specific PSAAP algorithm as compared to all-gene algorithm plotted to show sensitivity (8E), specificity (8F), and positive predictive value (PPV, FIG. 8G).
Figure 8F:
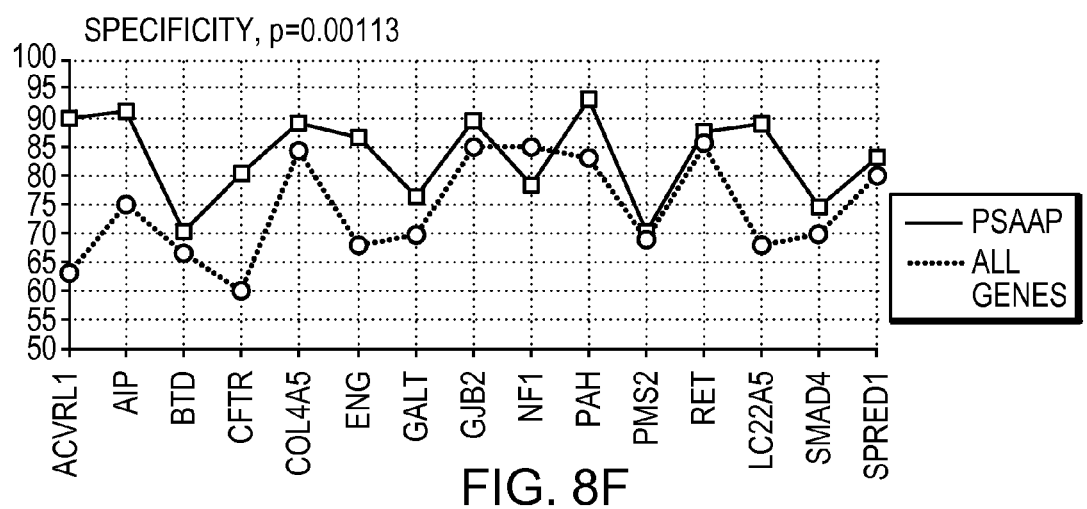
Figure 8G:
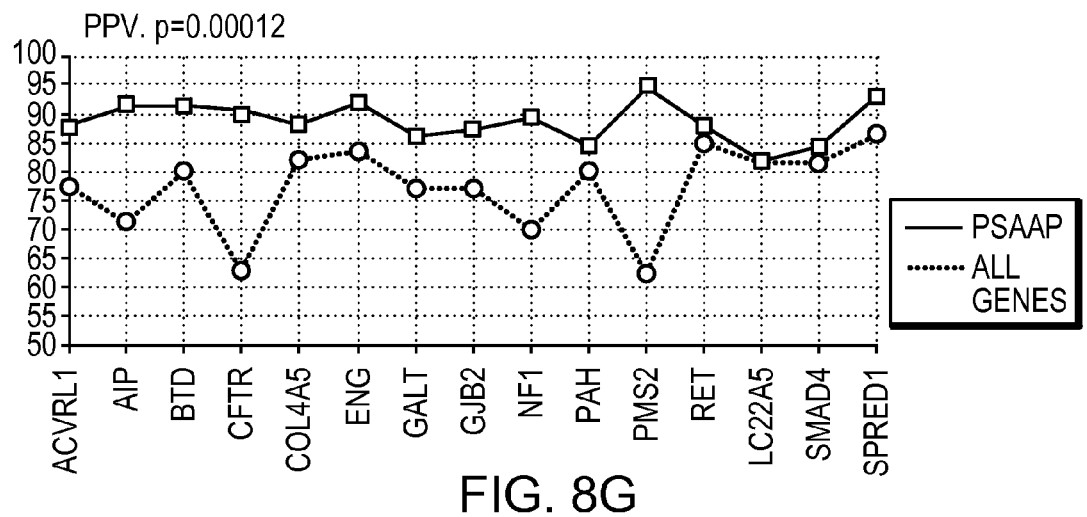

FIGS. 8E, 8F, 8G illustrate the performance of the gene-specific PSAAP algorithm as compared to all-gene algorithm plotted to show sensitivity (8E), specificity (8F), and positive predictive value (PPV, FIG. 8G). Overall, the performance of the PSAAP gene-specific trained algorithm is significantly better (8% to 13%) than the "all-gene" model, with p values of 0.00001 (sensitivity), 0.00113 (specificity) and 0.00012 (PPV), as shown in FIGS. 8E, 8F, and 8G. For the genes evaluated, the PPV of the gene-specific PSAAP algorithm averages 89% (82% to 94%). This is on average 11% higher than the "all-gene" model where PPV ranged from 62% to 86%. The one exception was SLC22A5, where PPV remaines constant. Sensitivity averaged 13% higher than the "all-gene" model, except for SPRED1 which was 6% decreased. Specificity is also generally improved (9% average) for all but PMS2 (no increase) and NF1, which is 5% decreased.

Figure 8H:
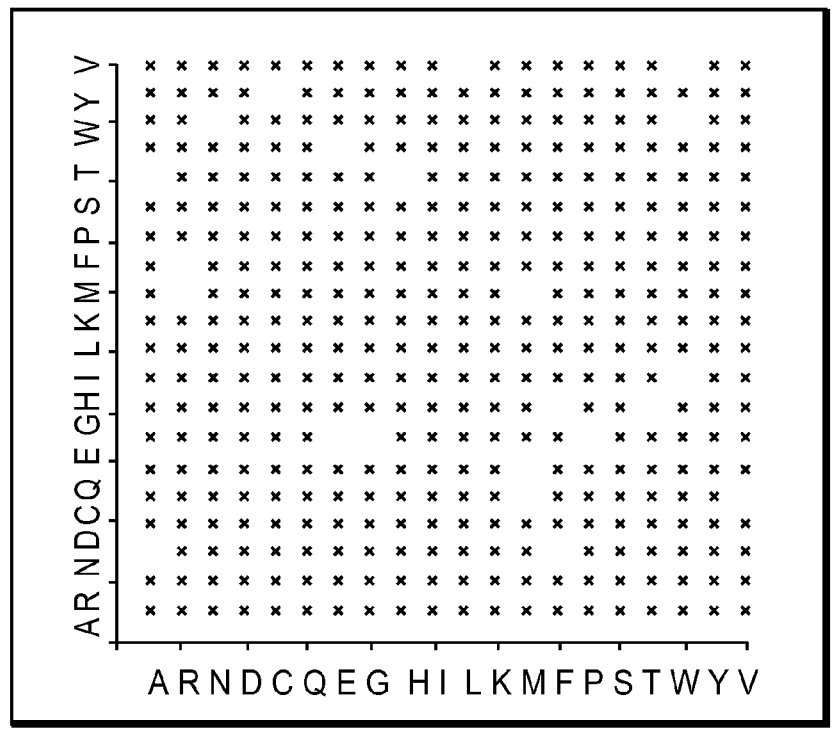
FIGS. 8H and 8I illustrate an example of specificity of pathogenic mutations.
Figure 8I:
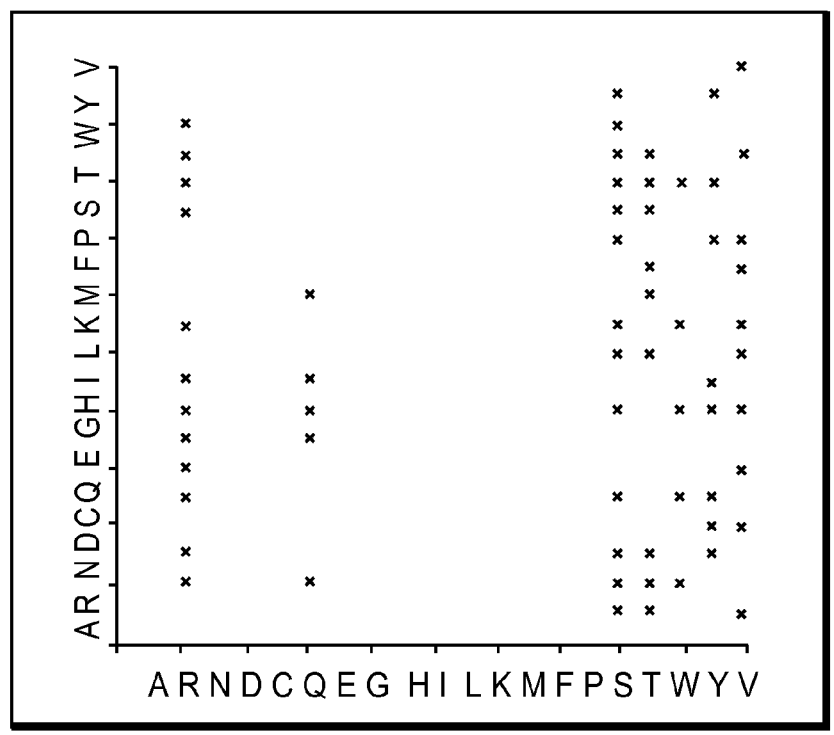

Examples of pecificity of pathogenic mutations demonstrated by plotting (FIG. 8H) simulated random amino acid substitutions (n=1000) showing a wide distribution that evenly covers the entire range of possible substitutions and known pathogenic mutations (FIG. 8I, n=1000) showing characteristic trends of specific residues and frequency of substitution. The improved performance of gene-specific algorithms may be explained in part by an important observation that biochemical and/or structural characteristics of mutation specific to one disease may be lost or diluted when combined with large genome-wide data sets for algorithm development. This may be illustrated by plotting non-synonymous variants specific to a gene-disease condition as compared to random amino acid substitutions (FIG. 8H and FIG. 8I). When 1000 random amino acid changes are plotted (FIG. 8H), a wide distribution evenly covers the entire range of possible substitutions. In contrast, when 1000 pathogenic mutations are graphed, characteristic trends of specific residues and frequency of substitution are readily seen (FIG. 8I).

Figure 8J:
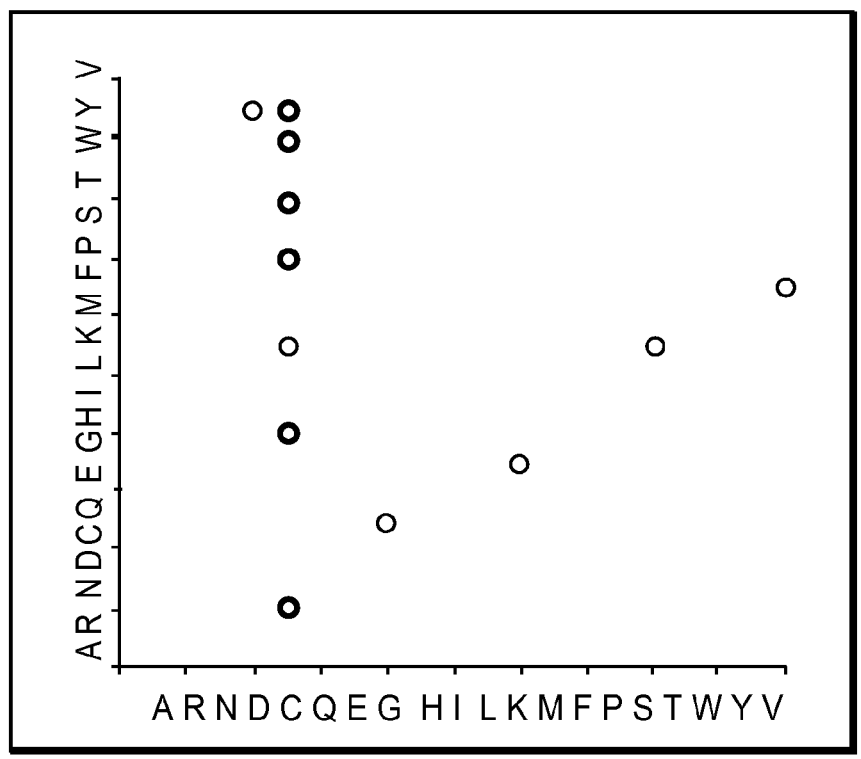
FIGS. 8J and 8K illustrate an example of disease specificity of pathogenic mutations.
Figure 8K:
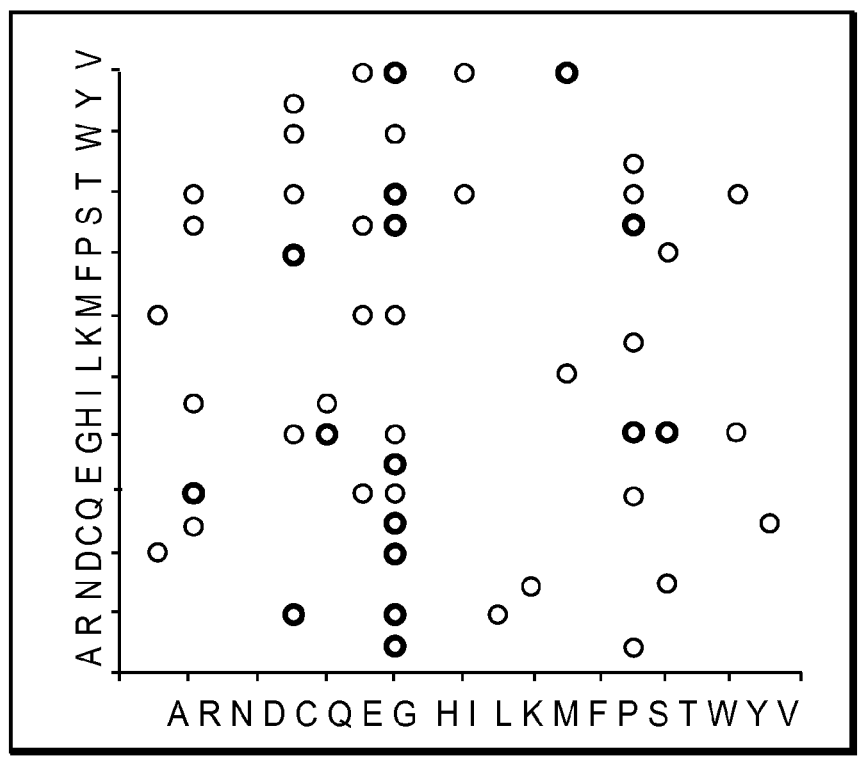

Disease-specific examples of this concept are shown in FIG. 8J and FIG. 8K. Disease specificity of pathogenic mutations are demonstrated by plotting the RET protooncogene variants where 79% of pathogenic changes are cysteine [C] to another residue [X] and (FIG. 8J) and COL4A5 where 84% pathogenic changes are glycine [G] to another residue [X] again showing characteristic trends of specific residues and frequency of substitution that may be lost when diluting gene-specific data into genome wide computational methods (FIG. 8K).

In the RET proto-oncogene (associated with medullary thyroid cancers), some 79% of all pathogenic changes were found to involve cysteine (C) to some other residue (X) as displayed in FIG. 8J. In the COL4A5 gene (associated with Alport syndrome), 84% of pathogenic changes involve glycine (G) to other residues (X) as shown in FIG. 8K.

FIG. 9A summarizes the performance of the PSAAP classifier, in classifying RET curated mutations with uncertain outcomes, and compares its performance to other methods available in the art. Specifically, evaluation of RET non-synonymous variants of unknown significance (VUS) mutations (n=46) is performed using the PSAAP algorithm. As shown, the PSAAP algorithm classifies 22 of the uncertain variants as pathogenic, while the remaining 24 fall within the benign grouping. For those variants classified as predicted pathogenic, the PSAAP algorithm estimated confidence remains above 90%.

Results from analysis of the RET uncertain gene variants (VUS) using the established on-line prediction tools are also summarized in FIG. 9A, with predicted pathogenic variants bolded and ranked by agreement. The MutPred tool calculates the probability of a deleterious mutation and corresponding hypothesis of disrupted molecular mechanism. In this example, theMutPred's default probability cutoff is set at 0.75 for differentiating between benign and disrupted/pathogenic mutations. The PSAAP algorithm agrees with MutPred in 16 benign and 8 pathogenic predictions for 52% agreement (24 out of 46). The PolyPhen has outcomes of "benign", "possibly damaging" and "probably damaging". The PSAAP classifier agrees with PolyPhen in 13 benign and 22 pathogenic predictions for 76% agreement (35 out of 46). The PMut yields outcomes of "pathological" or "neutral" and a corresponding reliability metric (lower is better). The PSAAP trained algorithm is in concordance with PMut in 13 benign and 14 pathogenic predictions for 58% agreement (27 out of 46). The SIFT algorithm gives outcomes of "tolerated" and "affects protein function". The PSAAP algorithm agrees with SIFT in 19 benign and 16 pathogenic predictions for 76% agreement (35 out of 46).

For predicted RET benign variants, 7 of 24 agree across all algorithms, while only 6 of 22 predicted pathogenic RET variants show agreement across the different methods. Although only 13 out of 46 (28%) are concordant, these variants may count as having a higher degree of confidence in prediction due to the varied methodologies and basis of classification. Importantly, the focus of molecular research and clinical efforts may, therefore, be directed to this prioritized listing of RET uncertain variants.

FIG. 9B is a table that includes the comparison outcome of selected RET mutations using PolyPhen, SIFT, and MutPred.

FIG. 10A illustrates a schematic of the RET protein with clinically curated variants. FIG. 10B illustrates a schematic of the RET protein with predicted disease association for uncertain variants mapped across protein location. The phenotype overlay shows regions of reported MEN2A, MEN2B and FMTC disease. Specifically, FIG. 10A visually highlights the cysteine rich region just prior to the transmembrane domain, and the transmembrane domain itself which contain the majority of pathogenic variants. The predictions obtained from the PSAAP classifier for the uncertain RET variants (VUS) are also mapped by location across the length of the protein and included in FIG. 10B.

Several unpublished RET gene variants with known pathological (MEN2) outcomes (n=5) are identified during routine genetic testing at ARUP Laboratories. To further benchmark a gold standard of truth for RET mutation prediction, all five algorithms are used to classify this set of not yet seen variants. The Bayesian trained PSAAP classifier 110 correctly identifies all five variants as pathogenic. PMut calls 3 disease causing variants correctly, but classifies two others as "neutral" mutations, when in fact these changes were known to be associated with disease. PolyPhen also correctly identifies 3 as probably damaging (pathogenic), but misses classified the same 2 variants as PMut. SIFT predicts 4 of these variants affect function (pathogenic), but calls one of the same variants "tolerated." MutPred correctly predicted all 5 as pathogenic.

The PSAAP classifier disclosed herein is trained specifically to curated RET disease outcomes. This is in contrast to the less robust curated collections of mutations, such as OMIM or dbSNP. Further, no homolog alignment or solved protein structure is necessary. Rather, the classifier relies on primary sequence information only, with calculated delta matrices of substituted amino acid properties, and is therefore not limited to scenarios where SIFT or PolyPhen (and others) are traditionally being used. These facts may explain the improved performance when classifying RET variants as compared to generalized prediction tools available on-line.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configuration of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

Various modifications may be made to the examples described in the foregoing, and any related teachings may be applied in numerous applications, only some of which have been described herein. It is intended by the following claims to claim any and all applications, modifications and variations that fall within the true scope of the present teachings.

What is claimed is:

1. A method of predicting a result of genetic mutation, comprising:
    determining differences between (i) values of a first plurality of features, of amino acids encoded by a variant of a wild-type polynucleotide sequence, and (ii) values of a second plurality of features, of amino acids encoded by the wild-type polynucleotide sequence;
    wherein the features of the first plurality are the same as the features of the second plurality; and
    by a processor and based on the differences, determining a predicted phenotype severity of the variant.

2. The method of claim 1, wherein the prediction includes an indication of a disease.

3. The method of claim 1, wherein at least one of the first plurality of features is selected from the group consisting of alpha NH chemical shifts, normalized frequency of C terminal helix, normalized frequency of chain reversal IR, normalized positional frequency at helix termini N2, partition coefficient Garel, relative preference value at C2, relative preference value at N1, weights for beta sheet at the window position of 0, amino acid distribution, average relative fractional occurrence in A0(i), average relative probability of inner beta sheet, composition, effective partition energy, free energy in alpha helical region, frequency of the third residue in turn, helix formation parameters (delta delta G), hydrophobicity, membrane buried preference parameters, normalized frequency of beta structure, normalized frequency of con, normalized positional frequency at helix termini Cc, STERIMOL maximum width of the side chain, and Zimm Bragg parameter sigma.

4. The method of claim 1, wherein at least one of the first plurality of features is selected from the group consisting of alpha NH chemical shifts, normalized frequency of C terminal helix, normalized frequency of chain reversal R, normalized positional frequency at helix termini N2, partition coefficient Garel, relative preference value at C2, relative preference value at N1, weights for beta sheet at the window position of 0, amino acid distribution, average relative fractional occurrence in A0(i), average relative probability of inner beta sheet, composition, effective partition energy, free energy in alpha helical region, frequency of the third residue in turn, helix formation parameters (delta delta G), hydrophobicity, membrane buried preference parameters, normalized frequency of beta structure, normalized frequency of coil, normalized positional frequency at helix termini Cc, STERIMOL maximum width of the side chain, and Zimm Bragg parameter sigma.

5. A method of predicting a result of genetic mutation, comprising:
    determining differences between (i) values of a first plurality of features, of amino acids encoded by a variant of a wild-type polynucleotide sequence, and (ii) values of a second plurality of features, of amino acids encoded by the wild-type polynucleotide sequence;
    wherein the features of the first plurality are the same as the features of the second plurality;
    by a processor, training a machine learning classification algorithm using the differences; and
    determining, by the trained algorithm, a prediction of phenotype severity of the gene variant.

6. The method of claim 5, wherein the machine learning classification algorithm includes at least one of Zero Rules (ZeroR), naive Bayesian, Simple Logistic Regression (Simple Logistic), Support Vector Machine (SMO), k-nearest neighbor (IBk), or Random Forest Regression (Random Forest).

7. The method of claim 5, wherein the plurality of features comprises at least one of physical, chemical, conformational, physiochemical, biochemical, or energetic properties of amino acids.

8. The method of claim 5, further including selecting the plurality of features by performing correlation-based feature subset selection and best-first greedy hill-climbing search and identifying a subset of properties that differentiate benign mutations from pathogenic mutations.

9. A non-transitory computer-readable medium encoded with machine-executable instructions for:
    determining differences between (i) values of a first plurality of features, of amino acids encoded by a variant of a wild-type polynucleotide sequence, and (ii) values of a second plurality of features, of amino acids encoded by the wild-type polynucleotide sequence;
    wherein the features of the first plurality are the same as the features of the second plurality; and
    by a processor and based on the differences, determining a predicted phenotype severity of the variant.

10. The method of claim 9, wherein the prediction includes an indication of a disease.

11. The method of claim 9, wherein at least one of the first plurality of features is selected from the group consisting of alpha NH chemical shifts, normalized frequency of C terminal helix, normalized frequency of chain reversal R, normalized positional frequency at helix termini N2, partition coefficient Garel, relative preference value at C2, relative preference value at N1, weights for beta sheet at the window position of 0, amino acid distribution, average relative fractional occurrence in A0(i), average relative probability of inner beta sheet, composition, effective partition energy, free energy in alpha helical region, frequency of the third residue in turn, helix formation parameters (delta delta G), hydrophobicity, membrane buried preference parameters, normalized frequency of beta structure, normalized frequency of coil, normal zed positional frequency at helix termini Cc, STERIMOL maximum width of the side chain, or Zimm Bragg parameter sigma.

12. The method of claim 9, wherein at least one of the first plurality of features is selected from the group consisting of alpha NH chemical shifts, normalized frequency of C terminal helix, normalized frequency of chain reversal R, normalized positional frequency at helix termini N2, partition coefficient Garel, relative preference value at C2, relative preference value at N1, weights for beta sheet at the window position of 0, amino acid distribution, average relative fractional occurrence in A0(i), average relative probability of inner beta sheet, composition, effective partition energy, free energy in alpha helical region, frequency of the third residue in turn, helix formation parameters (delta delta G), hydrophobicity, membrane buried preference parameters, normalized frequency of beta structure, normalized frequency of coil, normalized positional frequency at helix termini Cc, STERIMOL maximum width of the side chain, or Zimm Bragg parameter sigma.

13. A non-transitory computer-readable medium encoded with machine-executable instructions for:
   determining differences between (I) values of a first plurality of features, of amino acids encoded by a variant of a wild-type polynucleotide sequence, and (ii) values of a second plurality of features, of amino acids encoded by the wild-type polynucleotide sequence;
   wherein the features of the first plurality are the same as the features of the second plurality;
   training a machine learning classification algorithm using the differences; and
   determining, by the trained algorithm, a prediction of phenotype severity of the gene variant.

14. The method of claim 13, wherein the machine learning classification algorithm includes at least one of Zero Rules (ZeroR), naive Bayesian, Simple Logistic Regression (Simple Logistic), Support Vector Machine (SMO), k-nearest neighbor (lBk), or Random Forest Regression (Random Forest).

15. The method of claim 13, wherein the plurality of features comprises at least one of physical, chemical, conformational, physiochemical, biochemical, or energetic properties of amino acids.

16. The method of claim 13, further including selecting the plurality of features by performing correlation-based feature subset selection and best-first greedy hill-climbing search and identifying a subset of properties that differentiate benign mutations from pathogenic mutations.

* * * * *